(12) United States Patent
Traber et al.

(10) Patent No.: US 9,872,909 B2
(45) Date of Patent: Jan. 23, 2018

(54) METHOD FOR ENHANCING SPECIFIC IMMUNOTHERAPIES IN CANCER TREATMENT

(71) Applicants: Peter G. Traber, Duluth, GA (US); William L. Redmond, Hillsboro, OR (US); Eliezer Zomer, Newton, MA (US); Anatole Klyosov, Newton, MA (US); Stefanie N. Linch, Portland, OR (US)

(72) Inventors: Peter G. Traber, Duluth, GA (US); William L. Redmond, Hillsboro, OR (US); Eliezer Zomer, Newton, MA (US); Anatole Klyosov, Newton, MA (US); Stefanie N. Linch, Portland, OR (US)

(73) Assignees: Galeotin Therapeutics, Inc., Norcross, GA (US); Providence Health & Services—Oregon, Portland, OR (US)

(*) Notice: Subject to any disclaimer, the term of this patent is extended or adjusted under 35 U.S.C. 154(b) by 95 days.

(21) Appl. No.: 14/029,505

(22) Filed: Sep. 17, 2013

(65) Prior Publication Data
US 2014/0086932 A1    Mar. 27, 2014

Related U.S. Application Data

(60) Provisional application No. 61/701,914, filed on Sep. 17, 2012, provisional application No. 61/756,818, filed on Jan. 25, 2013, provisional application No. 61/759,532, filed on Feb. 1, 2013.

(51) Int. Cl.
| | |
|---|---|
| A61K 47/26 | (2006.01) |
| A61K 39/395 | (2006.01) |
| C07K 16/28 | (2006.01) |
| C07K 16/30 | (2006.01) |
| A61K 9/00 | (2006.01) |
| A61K 39/00 | (2006.01) |

(52) U.S. Cl.
CPC ............ *A61K 47/26* (2013.01); *A61K 9/0019* (2013.01); *A61K 39/39558* (2013.01); *C07K 16/2818* (2013.01); *C07K 16/2878* (2013.01); *C07K 16/3069* (2013.01); *A61K 2039/505* (2013.01)

(58) Field of Classification Search
CPC ............ C07K 16/2818; C07K 16/2878; C07K 16/3069; A61K 39/39558; A61K 9/0019; A61K 47/26; A61K 2039/505; A61K 2300/00
USPC ...................... 424/144.1, 174.1, 184.1, 277.1
See application file for complete search history.

(56) References Cited

U.S. PATENT DOCUMENTS

| | | | |
|---|---|---|---|
| 2,132,577 A | 10/1938 | Olsen et al. | |
| 2,444,266 A | 6/1948 | Maclay et al. | |
| 2,503,258 A | 4/1950 | Graham et al. | |
| 4,016,351 A | 4/1977 | Eschinasi et al. | |
| 4,268,533 A | 5/1981 | Williams et al. | |
| 4,686,106 A | 8/1987 | Ehrlich et al. | |
| 5,071,970 A | 12/1991 | le Grand et al. | |
| 5,498,702 A | 3/1996 | Mitchell et al. | |
| 5,681,923 A | 10/1997 | Platt | |
| 5,834,442 A | 11/1998 | Raz et al. | |
| 5,895,784 A | 4/1999 | Raz et al. | |
| 6,417,173 B1 | 7/2002 | Roufa et al. | |
| 6,423,314 B2 | 7/2002 | Platt et al. | |
| 6,500,807 B1 | 12/2002 | Platt et al. | |
| 6,632,797 B2 | 10/2003 | Siren | |
| 6,680,306 B2 | 1/2004 | Chang et al. | |
| 6,756,362 B2 | 6/2004 | Roufa et al. | |
| 6,770,622 B2 | 8/2004 | Jarvis et al. | |
| 6,890,906 B2 | 5/2005 | Chang et al. | |
| 7,491,708 B1 | 2/2009 | Platt et al. | |
| 7,893,252 B2 | 2/2011 | Platt et al. | |
| 8,128,966 B2 | 3/2012 | Staples et al. | |
| 8,187,642 B1 | 5/2012 | Staples et al. | |
| 8,236,780 B2 | 8/2012 | Platt et al. | |
| 8,409,635 B2 | 4/2013 | Staples et al. | |
| 8,420,133 B2 | 4/2013 | Staples et al. | |
| 8,658,787 B2* | 2/2014 | Traber et al. | .......... 536/123 |
| 8,828,971 B2 | 9/2014 | Traber et al. | |
| 8,871,925 B2* | 10/2014 | Zomer et al. | .......... 536/123 |
| 8,962,824 B2 | 2/2015 | Zomer et al. | |
| 9,339,515 B2 | 5/2016 | Traber | |
| 2003/0004132 A1 | 1/2003 | Chang et al. | |
| 2003/0013682 A1 | 1/2003 | Banito et al. | |
| 2004/0023925 A1 | 2/2004 | Chang et al. | |

(Continued)

FOREIGN PATENT DOCUMENTS

| | | | |
|---|---|---|---|
| JP | H07-109226 A | 4/1995 | |
| JP | 2001-519471 A | 10/2001 | |

(Continued)

OTHER PUBLICATIONS

De Smedt et al. Effect of interieukin-IO on dendritic cell maturation and function. Eur J Immunol 27:1229-1235, 1997.*
Driessens et al. Costimulatory and coinhibitory receptors in anti-tumor immunity. Immunol Rev 229:126-144, 2009.*
Erdman et al. CD4+CD25+ Regulatory Lymphocytes Induce Regression of Intestinal Tumors in ApcMin/+ Mice. Cancer Res 2005; 65(10): 3998-4004.*
Fracanzani et al. Contrast-Enhanced Doppler Ultrasonography in the Diagnosis of Hepatocellular Carcinoma and Premalignant Lesions in Patients With Cirrhosis. Hepatology 34:1109-1112, 2001.*
International Search Report and Written Opinion from International Application No. PCT/US2013/060182 dated Dec. 6, 2013.
Demotte et al., "A Galectin-3 Ligand Corrects the Impaired Function of Human CD4 and CD8 Tumor-Infiltrating Lymphocytes and Favor Tumor Rejection in Mice"; Cancer Res; 70(19) Oct. 1, 2010; pp. 7476-7488.

(Continued)

*Primary Examiner* — Yih-Horng Shiao
(74) *Attorney, Agent, or Firm* — Greenberg Traurig, LLP

(57) ABSTRACT

Methods and compositions of the invention relate to the enhancement of specific immunotherapies in cancer treatment. In particular, aspects of the invention relate to novel approaches to boost immune function using a complex carbohydrate pharmaceutical compound alone or in combination with other targeted immunotherapy to increase the efficacy of immunotherapy of cancer.

17 Claims, 18 Drawing Sheets

(56) References Cited

U.S. PATENT DOCUMENTS

| | | | |
|---|---|---|---|
| 2004/0043962 | A1 | 3/2004 | Chang et al. |
| 2004/0121981 | A1 | 6/2004 | Chang et al. |
| 2004/0223971 | A1 | 11/2004 | Chang et al. |
| 2005/0008572 | A1 | 1/2005 | Prokop et al. |
| 2006/0094688 | A1 | 5/2006 | Tanaka et al. |
| 2006/0211653 | A1 | 9/2006 | Ni |
| 2008/0089959 | A1 | 4/2008 | Chang et al. |
| 2008/0107622 | A1 | 5/2008 | Platt et al. |
| 2009/0217401 | A1 | 8/2009 | Korman et al. |
| 2011/0046086 | A1 | 2/2011 | Yun et al. |
| 2013/0261078 | A1 | 10/2013 | Zomer et al. |

FOREIGN PATENT DOCUMENTS

| | | | |
|---|---|---|---|
| JP | 2005-531576 | A | 10/2005 |
| WO | 85/05031 | A1 | 11/1985 |
| WO | 99/19365 | A1 | 4/1999 |
| WO | 03/099308 | A1 | 12/2003 |
| WO | 2004/091634 | A1 | 10/2004 |
| WO | 2005/095463 | A1 | 10/2005 |
| WO | 2013/101314 | A1 | 7/2013 |
| WO | 2013/184892 | A1 | 12/2013 |

OTHER PUBLICATIONS

Zhan et al., "Scarcity or complete lack of single rhamnose residues interspersed within the homogalacturonan regions of citrus pectin"; Carbohydrate Research 308 (1998), pp. 373-380.
Patra et al., "Structural characterization of an immunoenhancing heteropolysaccharide isolated from hot water extract of the fresh leaves of Catharanthus rosea"; Carbohydrate Polymers 81 (2010); pp. 584-591.
Patra et al., "Structure elucidation of an immunoenhancing pectic polysaccharide isolated from aqueous extract of pods of green bean (*Phaseolus vulgaris* L.)"; Carbohydrate Polymers 87 (2012); pp. 2169-2175.
Banh et al. "Tumor galectin-1 mediates tumor growth and metastasis through regulation of T-cell apoptosis", Cancer Res. 71:4423-31 (2011).
Barondes et al., "Galectins: a family of animal beta-galactoside-binding lectins [letter]", Cell. (76):597-598 (1994).
Barrow at al., "The role of galectins in colorectal cancer progression," Int. J. Cancer. 129:1-8 (2011b).
Cay et al., "Review Immunohistochemical expression of galectin-3 in cancer: a review of the literature," Patoloji Derg. 28(1): 1-10 (2012).
Forsman et al., "Galectin 3 aggravates joint inflammation and destruction in antigen-induced arthritis," Arthritis Reum. 63: 445-454 (2011).
Godwin Avwioro, "Histochemical Uses of Haematoxylin—A Review," JPCS. 1: 24-34 (2011).
Kolatsi-Joannou et al., "Modified citrus pectin reduces galectin-3 expression and disease severity in experimental acute kidney injury," PLoS One. 6: e18683, doi:10.1371/journal.pone.0018683 (2011).
Lefranc et al., "Galectin-1 mediated biochemical controls of melanoma and glioma aggressive behavior," World J. Biol. Chem. 2: 193-201 (2011).
Liu et al., "Galectins in regulation of inflammation and immunity," In Galectins (ed. by Kiyosov, A.A., Witzhak, Z.A., and Platt, D.), John Wiley & Sons, Hoboken, New Jersey, pp. 97-113 (2008).
Lopez et al., "Gene expression profiling in lungs of chronic asthmatic mice treated with galectin-3: downregulation of inflammatory and regulatory genes," Mediators Inflamm., 823279. Epub Mar. 20, 2011 (2011).
Newlaczyl et al., "Galectin-3—a jack-of-all-trades in cancer," Cancer Lett. 313: 123-128 (2011).
Ohshima et al., "Galectin 3 and its binding protein in rheumatoid arthritis," Arthritis Rheum. 48: 2788-2795 (2003).
Sato et al., "Galectins as danger signals in host-pathogen and host-tumor interactions: new members of the growing group of Alarmins." In "Galectins," (Klyosov, et al eds.), John Wiley and Sons, 115-145 (2008).
Toussaint et al., "Galectin-I, a gene preferentially expressed at the tumor margin, promotes glioblastoma cell invasion", Mol Cancer. 11:32. (2012).
Wang et al., "Nuclear and cytoplasmic localization of galectin-1 and galectin-3 and their roles in pre-mRNA splicing." In "Galectins" (Klyosov et al eds.), John Wiley and Sons, 87-95 (2008).
Trisha Gura; Science, vol. 278, Nov. 7, 1997, 1041-1042.
Sun et al., "Structural characterization of a tobacco rhamnogalacturonan", Carbohydrate Polymers, Applied Science Publishers, Ltd. Barking, GB, vol. 7, No. 2, Jan. 1, 1987, pp. 143-158.
Lamichhane et al., "PD-1 abd IL-10: partners in crime against anti-tumor immunity in ovarian cancer", The Journal of Immunology, May 1, 2015 vol. 194, No. 1.
Park et al., "Diverse Roles of Invariant Natural Killer T Cells in Liver Injury and Fibrosis Induced by Carbon Tetrachloride", Hepatology, May 2009; 49(5), pp. 1683-1694.
English language translation of the Notification of the First Office Action from Chinese Patent Application No. 201380054287.X dated Apr. 28, 2016.
Demotte et al., "Restoring the Association of the T Cell Receptor with CD8 Reverses Anergy in Human Tumor-Infiltrating Lymphocytes", Immunity 28, pp. 414-424 Mar. 2008.

\* cited by examiner

Figure 8.
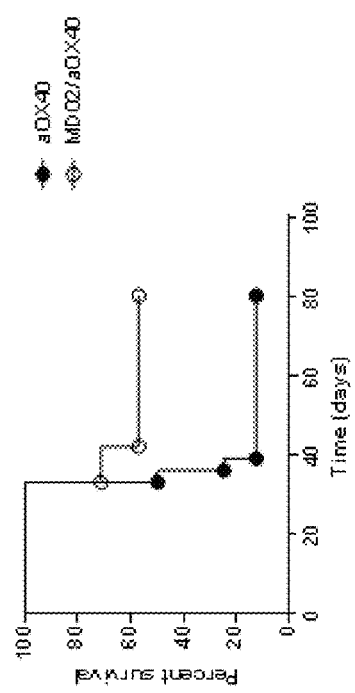
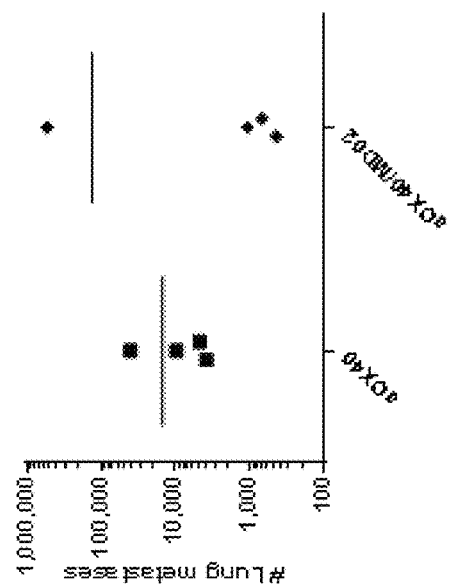

METHOD FOR ENHANCING SPECIFIC IMMUNOTHERAPIES IN CANCER TREATMENT

RELATED APPLICATIONS

This application claims the benefit of and priority to U.S. Provisional Application Ser. No. 61/701,914, filed Sep. 17, 2012, U.S. Provisional Application Ser. No. 61/756,818, filed Jan. 25, 2013, and U.S. Provisional Application Ser. No. 61/759,532, filed Feb. 1, 2013, the entire disclosure of each of which is incorporated herein by reference in their entireties.

FIELD OF THE INVENTION

Methods and compositions of the invention relate to the enhancement of specific immunotherapies in cancer treatment.

BACKGROUND OF THE INVENTION

The immune system recognizes foreign antigens and orchestrates a coordinated response involving multiple cell types that results in eliminating the foreign antigens or the pathogen or cell that expresses the foreign antigens. The immune system is crucial for protection from invading microorganisms, including but not limited to bacteria, viruses, and parasites and surveillance for and removal of abnormal or mutated cells (cancer). This system also provides an obstacle in therapeutic interventions by reaction to insertion of medical devices into the body or transplantation of heterologous organs or cells.

In addition to the baseline functions of the immune system in protecting the host animal, there is great promise for modulating the immune system for the benefit of treating disease. In this regard, harnessing the patient's own immune system to attack and treat the patient's cancer can be a very promising therapeutic approach for many different types of cancer.

Despite recent successes of immunotherapy for treatment of cancer, the response of human tumors is variable among individuals and in those where it works, it is often only partially successful.

There is a need, therefore, for approaches that can enhance the ability of immunotherapies to treat cancers.

SUMMARY OF THE INVENTION

Aspects of the invention relate to novel approaches to boost immune function using a complex carbohydrate pharmaceutical compound alone or in combination with other targeted immunotherapy that may increase the efficacy of immunotherapy of cancer.

Aspects of the invention relate to compositions, methods of using and methods of manufacturing compositions capable of boosting the immune function.

Other aspects of the invention relate to methods of treating a subject in need thereof. In some embodiments, the method comprises the step of obtaining a composition for intravenous, subcutaneous, other routes of parenteral, or oral administration, the composition comprising a compound in an acceptable pharmaceutical carrier and administering the composition to a subject in need thereof.

In some embodiments, the compound can be one of galacto-rhamnogalacturonate (GRG), galactoarabino-rhamnogalacturonate (GA-RG), galactomannan (GM), modified synthetic disaccharides (MSD), peptide/protein inhibitor agents (PIA), peptidomimetic agents (PMA), galectin-specific antibodies (GSA) or small organic molecules (SOM) or a combination of any of the foregoing.

In some embodiments, the specific GRG, GA-RG, GM, MSD, PIA, PMA, GSA, or SOM compounds can have the ability to interact with various domains of the class of galectin proteins, which includes galectins 1 through 15, and thereby inhibit, enhance or modulate their function.

In some embodiments, the specific GRG, GA-RG, GM, MSD, PIA, PMA, GSA, or SOM compounds can have the ability to interact with various domains of the galectin-3 protein, including but not limited to the S- and F-face of the carbohydrate recognition domain and the N-terminal domain, and thereby inhibit its interaction with natural ligands which inhibits galectin-3 function.

In some embodiments, the specific GRG, GA-RG, GM, MSD, PIA, PMA, GSA, or SOM compounds can have the ability to interact with various domains of the galectin-1 protein, including but not limited to the carbohydrate recognition domain and the dimerization domain, and thereby inhibit its interaction with natural ligands which inhibits galectin-1 function.

In some embodiments, the compound can be a polysaccharide chemically defined as galacto-rhamnogalacturaonate (GRG), a selectively depolymerized branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-b-D-galactose (Gal) with lesser amounts of 1,5-a-L-arabinose (Ara) residues. Other side chain minor constituents may include xylose (Xyl), glucose (Glu), and fucose (Fuc) or combinations thereof.

In some embodiments, the GRG compound can be produced as described in U.S. Patent Application Publication No. 2008/0107622, now U.S. Pat. No. 8,236,780, which is incorporated expressly by reference for all purposes.

In some embodiments, the GRG compound can be produced as described in U.S. Pat. Nos. 8,128,966, 8,187,624, U.S. Patent Application Publication Nos 2012/0315309 and 2012/0309711 which are incorporated expressly by reference for all purposes.

In some embodiments, the compound can be a polysaccharide chemically defined as galactoarabino-rhamnogalacturonate (GA-RG), a selectively depolymerized, branched heteropolymer whose backbone is predominantly comprised of 1,4-linked galacturonic acid (GalA) and methyl galacturonate (MeGalA) residues, with a lesser backbone composition of alternating 1,4-linked GalA and 1,2-linked rhamnose (Rha), which in-turn is linked to any number of side chains, including predominantly 1,4-b-D-galactose (Gal) and 1,5-a-L-arabinose (Ara) residues. Other side chain minor constituents may include xylose (Xyl), glucose (Glu), and fucose (Fuc) or combinations thereof.

Aspects of the invention relate to methods comprising (a) obtaining a composition for parenteral or enteral administration comprising a galactoarabino-rhamnogalacturonate comprising a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof, and a therapeutically effective amount of an immune modulatory agent; in an acceptable pharmaceutical carrier; and (b) administering to a subject in need thereof an effective dose of the composition that results in one or more of the following: at least 10% increase in the activation of CD8+ T-cells, CD4+ T-cells, or CD8+ T-cells and CD4+ T-cells, at least 10% increase of tumor-antigen specific CD8+ or CD4+ T-cells; at least 10% decrease in tumor size, at least 10% decrease in size of metastases, at least a 10% decrease in number of metastases, a reduction of total tumor burden when compared to a control subject treated with the therapeutically effective amount of the immune modulatory agent alone. In some embodiments, the subject in need thereof is a subject having cancer. In some embodiments, the step of administering results in at least a 50% reduction of the total tumor burden in the subject so as to treat cancer.

In some embodiments, in the step of obtaining the galactoarabino-rhamnogalacturonate, the 1,4-linked galacturonic acid and methyl galacturonate residues backbone can represent between 55 to 85 molar percent of the total carbohydrate molar content, the branched heteropolymer of alternating a α-1,2 linked rhamnose and a α-1,4-linked GalA residues can represent between 1 and 6 molar percent of the total carbohydrate molar content, the oligomer 1,4-β-D-galactose of the primary branching can represent between 6 to 15 molar percent of the total carbohydrate molar content and the oligomer 1,5-α-L-arabinose of the primary branching can represent between 2 to 8 molar percent of the total carbohydrate molar content, as characterized by gas chromatography/mass spectrometry.

In some embodiments, the galactoarabino-rhamnogalacturonate can have an average molecular weight ranging from 20 kDa to 70 kDa. In some embodiments, the galactoarabino-rhamnogalacturonate further comprises xylose, glucose, fucose residues or combination thereof.

In some embodiments, the compound can be a peptide/protein inhibitor agent (PIA) that may bind to galectin and inhibit galectin function. In some embodiments, the peptide/protein inhibitor agent can include, but not limited to anginex. Anginex can be produced, in some embodiments, as described in U.S. Pat. No. 6,770,622, which is incorporated expressly by reference for all purposes.

In some embodiments, the compound can be a peptidomimetic agent (PMA) that can bind to galectin and inhibit galectin function. In some embodiments the PMA can be, but is not limited to OTX-008 (also known as PTX-008). In some embodiments, the peptidomimetic agent can include, but not limited to, the PMA produced as described in U.S. Pat. No. 8,207,228, which is incorporated expressly by reference for all purposes.

In some embodiments, the compound can be a galectin-specific antibody (GSA), including but not limited to a monoclonal antibody that binds to and inhibits galectin-3 or other members of the galectin family of proteins.

In some embodiments, the compound can be a small organic molecule (SOM) that can interact with various domains of galectin molecules including, but not limited to, the carbohydrate binding domain and the protein dimerization domain.

In some embodiments, the GRG, GA-RG, GM, MSD, PIA, PMA, GSA, or SOM compounds described herein can be used in combination with a therapeutically effective amount of monoclonal antibody, peptide or other agent that binds to lymphocyte co-stimulatory ligands or receptors and act as either antagonists or agonists of co-stimulation. Co-stimulatory receptors can include, but are not limited to, CD28 and ICOS. Co-stimulatory ligands can include, but are not limited to, CD80, CD86, and ICOS ligand.

In some embodiments, the GRG, GA-RG, GM, MSD, PIA, PMA, GSA, or SOM compounds described herein can be used in combination with a therapeutically effective amount of monoclonal antibody, peptide or other agent that binds to lymphocyte inhibitory ligands or receptors and act as either antagonists or agonists of lymphocyte inhibition. Inhibitory receptors can include, but are not limited to, CTLA-4 and LAG-3 (Lymphocyte-activation gene 3; also designated as CD223). Inhibitory ligands can include, but are not limited to, CD80 and CD86.

In some embodiments, the GRG, GA-RG, GM, MSD, PIA, PMA, GSA, or SOM compounds described herein can be used in combination with a therapeutically effective amount of monoclonal antibody that binds to CTLA-4 (anti-CTLA4).

In some embodiments, the GRG, GA-RG, GM, MSD, PIA, PMA, GSA, or SOM compounds described herein can be used in combination with a therapeutically effective amount of monoclonal antibody, peptide or other agent that binds to the tumor necrosis factor receptor (TNFR) superfamily of receptors or their ligands which are expressed on lymphocytes and act as either antagonists or agonists of lymphocyte co-stimulation. Members of the TNFR superfamily of receptors can include, but are not limited to, CD134, also known as OX40, CD27, and 4-1 BB and TNFR receptor ligands which include but are not limited to OX40L and CD70, and 4-1BBL (CD137L).

In some embodiments, the GRG, GA-RG, GM, MSD, PIA, PMA, GSA, or SOM compounds described herein can be used in combination with a therapeutically effective amount of monoclonal antibody that binds to OX40 (anti-OX40). In some embodiments, the GA-RG or GM compounds described herein can be used in combination with a therapeutically effective amount of recombinant OX40L or other agonists of OX40.

In some embodiments, the GRG, GA-RG, GM, MSD, PIA, PMA, GSA, or SOM compounds described herein can be used in combination with a therapeutically effective amount of monoclonal antibody that binds to PD-ligands (anti-PD-L1 and PD-L2).

In some embodiments, the GRG, GA-RG, GM, MSD, PIA, PMA, GSA, or SOM compounds described herein can be used in combination with a therapeutically effective amount of monoclonal antibody that binds to PD-1 (anti-PD-1).

In some embodiments, the GRG, GA-RG, GM, MSD, PIA, PMA, GSA, or SOM compounds described herein can be used in combination with a therapeutically effective amount of monoclonal antibody, peptide or other agent(s) that modifies activation or function of dendritic cells thereby altering antigen processing or response.

In some embodiments, the GRG, GA-RG, GM, MSD, PIA, PMA, GSA, or SOM compounds described herein can be used in combination with a therapeutically effective amount of a cancer vaccine. In some embodiments, the GRG, GA-RG, GM, MSD, PIA, PMA, GSA, or SOM compounds described herein can be used in combination with a therapeutically effective amount of a tumor-antigen directed vaccine.

In some embodiments, the GRG, GA-RG, GM, MSD, PIA, PMA, GSA, or SOM compounds described herein can be used in combination with a therapeutically effective amount of a vaccine used for the purpose of treating or preventing an infectious disease.

In some aspect of the invention, the method of treating cancer comprises (a) obtaining a composition for parenteral or enteral administration comprising a galactoarabino-rhamnogalacturonate in an acceptable pharmaceutical carrier, the galactoarabino-rhamnogalacturonate comprising a 1,4-linked galacturonic acid (GalA) and methyl galacturonate (MeGalA) residues backbone linked to branched heteropolymers of alternating oligomers of a α-1,2 linked rhamnose and a α-1,4-linked GalA residues, the rhamnose residues carrying a primary branching of oligomers of 1,4-β-D-galactose residues, 1,5-α-L-arabinose residues, or combinations thereof; and (b) administering to a subject in need thereof an effective dose of the composition that can result in at least one of the following: at least 10% increase in the activation of CD8+ T-cells, CD4+ T-cells, or CD8+ T-cells and CD4+ T-cells, at least 10% increase of tumor-antigen specific CD8+ or CD4+ T-cells; at least 10% decrease in tumor size, at least 10% decrease in size of metastases, at least a 10% decrease in number of metastases, a reduction of total tumor burden when compared to a control subject treated with a therapeutically effective amount of an approved therapy for the treatment of the cancer. In some embodiments, the step of administering can result in at least a 50% reduction of the total tumor burden in the subject so as to treat cancer.

In some embodiments, in the step of obtaining the galactoarabino-rhamnogalacturonate, the 1,4-linked galacturonic acid and methyl galacturonate residues backbone can represent between 55 to 85 molar percent of the total carbohydrate molar content, the branched heteropolymer of alternating a α-1,2 linked rhamnose and a α-1,4-linked GalA residues can represent between 1 and 6 molar percent of the total carbohydrate molar content, the oligomer 1,4-β-D-galactose of the primary branching can represent between 6 to 15 molar percent of the total carbohydrate molar content and the oligomer 1,5-α-L-arabinose of the primary branching can represent between 2 to 8 molar percent of the total carbohydrate molar content, as characterized by gas chromatography/mass spectrometry.

In some embodiments, the galactoarabino-rhamnogalacturonate can have an average molecular weight ranging from 20 kDa to 70 kDa. In some embodiments, the galactoarabino-rhamnogalacturonate can further comprise xylose, glucose, fucose residues or combination thereof.

In some aspect of the invention, the method comprises (a) obtaining a composition for parenteral or enteral administration comprising: (i) one of galacto-rhamnogalacturonate (GRG), galactoarabino-rhamnogalacturonate (GA-RG), galactomannan (GM), modified synthetic disaccharides (MSD), peptide/protein inhibitor agents (PIA), peptidomimetic agents (PMA), galectin-specific antibodies (GSA) or small organic molecules (SOM) or a combination of any of the foregoing, and (ii) a therapeutically effective amount of an immune modulatory agent wherein the immune modulatory agent comprises a monoclonal antibody, peptide, agent capable of binding to one or more of lymphocyte co-stimulatory ligands or receptors, lymphocyte inhibitory ligands or receptors, tumor necrosis factor receptor (TNFR) superfamily of receptors, PD-ligands or a combination of any of the foregoing; wherein the composition is in an acceptable pharmaceutical carrier. The method further comprises administering to a subject in need thereof an effective dose of the composition that can result in at least one of the following: at least 10% increase in the activation of CD8+ T-cells, CD4+ T-cells, or CD8+ T-cells and CD4+ T-cells, at least 10% increase of tumor-antigen specific CD8+ or CD4+ T-cells; at least 10% decrease in tumor size, at least 10% decrease in size of metastases, at least a 10% decrease in number of metastases. a reduction of total tumor burden when compared to a control subject treated with the therapeutically effective amount of the immune modulatory agent alone. In some embodiments, the step of administering can result in at least a 50% reduction of the total tumor burden in the subject so as to treat cancer.

In some embodiments, the immune modulatory agent can be an anti-OX40, anti-CTLA-4, anti-PD-1, anti PD-L2, antibody to 4-1BB/4-1BBL, antibody to LAG-3, or a combination thereof.

Other aspects of the invention relate to composition for parenteral administration, wherein the composition is in an acceptable pharmaceutical carrier and comprises (a) a therapeutically effective amount of a galactoarabino-rhamnogalacturonate comprising a 1,4-linked galacturonic acid (GalA) and methyl galacturonate (MeGalA) residues backbone linked to branched heteropolymers of alternating oligomers of a α-1,2 linked rhamnose and a α-1,4-linked GalA residues, the rhamnose residues carrying a primary branching of oligomers of 1,4-β-D-galactose residues, 1,5-α-L-arabinose residues, or combinations thereof, and (b) a therapeutically effective amount of an immune modulatory agent. In some embodiments, the composition can be used in the treatment of cancer.

In some embodiments, the immune modulatory can comprise a monoclonal antibody, peptide, agent capable of binding to one or more of lymphocyte co-stimulatory ligands or receptors, lymphocyte inhibitory ligands or receptors, tumor necrosis factor receptor (TNFR) superfamily of receptors, PD-ligands or a combination of any of the foregoing. In some embodiments, the immune modulatory agent can be an anti-OX40, anti-CTLA-4, anti-PD-1, anti PD-L2, antibody to 4-1BB/4-1BBL, antibody to LAG-3, or a combination thereof.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

FIG. 8A depicts survival in experiments using 4T1 mammary carcinoma tumors in mice with therapy with aOX40 alone or in combination with GA-RG (labeled as MD02). FIG. 8B depicts lung metastases in experiments using 4T1 mammary carcinoma tumors in mice with therapy with aOX40 alone or in combination with GA-RG (labeled as MD02).

FIG. 13A shows percent of OT-I positive/total CD8 cells in wild type and gal-3 null animals. FIG. 13B shows differences in expression of markers in wild type and gal-3 null CD8 lymphocytes. FIG. 13C shows differences in cytokine secretion in wild type and gal-3 null CD8 lymphocytes.

FIG. 14A is a graphical representation of several genes found to be down-regulated in Gal 3−/− OT-I cells over wild type cells. FIG. 14B shows the relative units and fold changes for selected genes FIG. 15 depicts that galectin-3 deficient CD8T cells have reduced CD25 and OX40 expression following antigen stimulation.

FIG. 16A-B depicts that galectin-3 inhibition using GA-RG (labeled as GR-MD-02 in this Figure) augments CD8 T cell expansion and effector function.

DETAILED DESCRIPTION OF THE INVENTION

Figure 1:
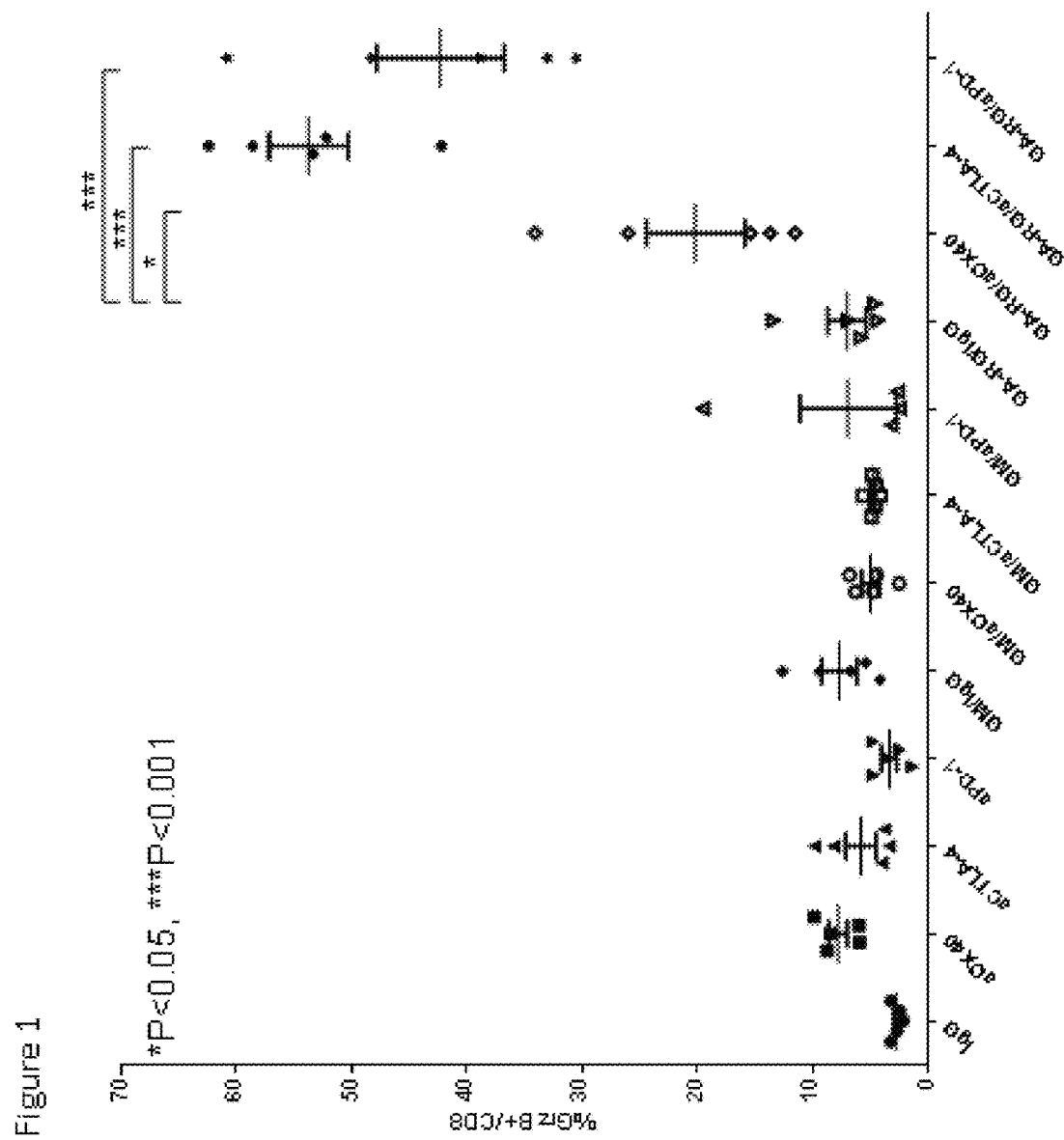
FIG. 1 depicts the percentage of peripheral blood lymphocytes from different experimental groups analyzed for the percent of CD8+ cells that express granzyme B.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Unless otherwise specified, all percentages expressed herein are weight/weight.

The term "subject" refers to an animal, including, but not limited to, a primate (e.g., human). The terms "subject" and "patient" are used interchangeably herein in reference, for example, to a mammalian subject, such as a human subject.

One approach that has been pursued for cancer immunotherapy is the area covered by the term "tumor vaccines" which includes immunization with tumor specific or over-expressed antigens. In this approach, an antigen or antigens specific for, or overexpressed in, tumor cells are injected alone, with adjuvants, as part of a microorganism that delivers the antigen (for example, Listeria Monocytogenes), or after incubation ex-vivo with immune cells (including but not limited to dendritic cells) in order to elicit cellular and/or humoral immune responses.

Another approach that has been pursued for cancer immunotherapy is through modulating the function of specific immune cell receptors or their ligands. This has been accomplished using monoclonal antibodies that recognize and bind to the immune cell receptors and/or ligands. The binding of the monoclonal antibody to the target receptor or ligand has been shown to either inhibit or enhance the function of that receptor or ligand.

Monoclonal antibodies that have been found to enhance the immune response to tumors include antibodies that bind CTLA-4 (cytotoxic T-lymphocyte-associated antigen-4), PD-1 receptor (programmed death-1), and OX40 (also known as CD134). In addition to their activity in cellular experiments and animals with tumors, anti-CTLA-4 and anti-PD-1 monoclonal antibodies have been shown to have important antitumor activity in humans.

Aspects of the invention relate to novel approaches to boost immune function using a complex carbohydrate pharmaceutical product or other agents described herein, alone or in combination with other targeted immunotherapy that may increase the efficacy of immunotherapy of cancer and other diseases which utilize activation of the immune system. The term "targeted immunotherapy" and "immune modulatory agent" are used interchangeably.

Some aspects of the invention relate to methods of treating a subject in need thereof. In some embodiments, the method comprises the step of obtaining a composition for intravenous, subcutaneous, other routes of parenteral, or oral administration, the composition comprising a compound in an acceptable pharmaceutical carrier and administering the composition to a subject in need thereof. In some embodiments, the composition comprises a compound and an immune modulatory agent in an acceptable pharmaceutical carrier.

Other aspects of the invention relate to a formulation for parenteral administration, wherein the formulation is in an acceptable pharmaceutical carrier and comprises a therapeutically effective amount of a compound and a therapeutically effective amount of an immune modulatory agent.

In some embodiments, the compound can be one of galacto-rhamnogalacturonate (GRG), galactoarabino-rhamnogalacturonate (GA-RG), galactomannan (GM), modified synthetic disaccharides (MSD), peptide/protein inhibitor agents (PIA), peptidomimetic agents (PMA), galectin-specific antibodies (GSA) or small organic molecules (SOM) or a combination of any of the foregoing.

In some embodiments, the specific GRG, GA-RG, GM, MSD, PIA, PMA, GSA, or SOM compounds can have the ability to interact with various domains of the class of galectin proteins, which includes galectins 1 through 15, and thereby inhibit, enhance or modulate their function.

In some embodiments, the specific GRG, GA-RG, GM, MSD, PIA, PMA, GSA, or SOM compounds can have the ability to interact with various domains of the galectin-3 protein, including but not limited to the S- and F-face of the carbohydrate recognition domain and the N-terminal domain, and thereby inhibit its interaction with natural ligands which inhibits galectin-3 function.

In some embodiments, the specific GRG, GA-RG, GM, MSD, PIA, PMA, GSA, or SOM compounds can have the ability to interact with various domains of the galectin-1 protein, including but not limited to the carbohydrate recognition domain and the dimerization domain, and thereby inhibit its interaction with natural ligands which inhibits galectin-1 function.

The term "effective dose" means the amount of the GRG, GA-RG, GM, MSD, PIA, PMA, GSA, or SOM compounds described herein in combination with one or more antibodies, proteins or other agents that modulate immune responses when administered as a parental dose to an animal or human with at least 10%, at least 20% or at least 25% enhancement of markers of immune response. Markers of the immune response include, but are not limited to, proliferation of T lymphocytes having a CD8 receptor, referred herein as CD8 lymphocytes (as indicated by various methods including, but not limited to, staining for Ki-67), markers of activated function of CD8 cells (as indicated by various methods including but not limited to staining for granzyme B), or changes in other cellular regulatory or effector cells. Other immune markers include but are not limited to the relative expression and/or frequency of GR-1+ and CD11b+ mononuclear cells.

Immune modulatory agents may include, but are not limited to, antibodies to OX40 (anti-OX40), antibodies to CTLA-4 (anti-CTLA-4), antibodies to PD-1 (anti-PD-1), antibodies to PD-1L/2L (anti-PD-L1 or anti-PD-L2), antibodies to 4-1BB/4-1BBL, antibodies to LAG-3, or a combination of two or more of the foregoing antibodies.

Immune modulatory agents also may include antibodies, proteins, peptides, or small organic molecules that affect processes of immune response, such as antigen-dependent recognition, antigen processing, lymphocyte co-stimulation, and lymphocyte inhibition.

The term "efficacy" means demonstrating a reduction of tumor growth, progression or metastasis of at least 10% using treatment with the GRG, GA-RG, GM, MSD, PIA, PMA, GSA, or SOM compounds described herein either alone or in combination with immune modulatory agents, or a combination of two or more of these agents, as compared to treatment with the immune modulatory agents alone, or a combination of two or more of these agents.

Aspects of the invention relate to compositions and methods of using compositions capable of boosting the immune function.

Aspects of the invention relate to methods of treating a subject in need thereof. In some embodiments, the subject is suffering from cancer. In some embodiments, the method comprises the step of obtaining a composition for intravenous or subcutaneous or oral administration comprising a compound in an acceptable pharmaceutical carrier. In some embodiments, the method comprises the step of obtaining a composition for parenteral administration. "Parenteral Administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In some embodiments, the compound is a polysaccharide chemically defined as galacto-rhamnogalacturaonate (GRG), a selectively depolymerized, branched heteropolymer whose backbone is predominantly comprised of 1,4-linked galacturonic acid (GalA) moieties and methyl galacturonate (MeGalA) residues, with a lesser backbone composition of alternating 1,4-linked GalA and 1,2-linked rhamnose (Rha), which in-turn is linked to any number of side chains, including predominantly 1,4-b-D-galactose (Gal) and 1,5-a-L-arabinose (Ara) residues. Other side chain minor constituents may include xylose (Xyl), glucose (Glu), and fucose (Fuc) or combinations thereof.

In some embodiments, the GRG compound is produced as described in U.S. Patent Application Publication No. 2008/0107622, now U.S. Pat. No. 8,236,780, which are incorporated expressly by reference for all purposes.

In some embodiments, the GRG compound can be produced as described in U.S. Pat. Nos. 8,128,966, 8,187,624, U.S. Patent Application Publication Nos 2012/0315309 and 2012/0309711 which are incorporated expressly by reference for all purposes.

In some embodiments, the compound is a polysaccharide chemically defined as galactoarabino-rhamnogalacturonate (GA-RG), a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-b-D-galactose (Gal) and 1,5-a-L-arabinose (Ara) residues. In some embodiments, the 1,4-linked galacturonic acid and methyl galacturonate residues backbone represents between 55 to 85 molar percent of the total carbohydrate molar content, the branched heteropolymer of alternating a $\alpha$-1,2 linked rhamnose and a $\alpha$-1,4-linked GalA residues represents between 1 and 6 molar percent of the total carbohydrate molar content, the oligomer 1,4-$\beta$-D-galactose of the primary branching represents between 6 to 15 molar percent of the total carbohydrate molar content and the oligomer 1,5-$\alpha$-L-arabinose of the primary branching represents between 2 to 8 molar percent of the total carbohydrate molar content, as characterized by gas chromatography/mass spectrometry.

Other side chain minor constituents may include xylose (Xyl), glucose (Glu), and fucose (Fuc) or combinations thereof.

In some embodiments, the molar percent of the 1,4-b-D-Gal and 1,5-a-L-Ara residues in the GA-RG compound of the present invention is 21.5% with a molar ratio of 3:1 of 1,4-b-D-Gal to 1,5-a-L-Ara.

In some embodiments, the compound is a polysaccharide chemically defined as galactoarabino-rhamnogalacturonate (GA-RG), with a molecular weight range of 20,000 to 70,000 Daltons as determined by SEC-RI method. In some embodiments, the galactoarabino-rhamnogalacturonate has an average molecular weight ranging from 20 kDa to 70 kDa.

In some embodiments, the GA-RG compound can be produced as described in International Patent Application PCT/US12/55311, which is incorporated expressly by reference for all purposes. In some embodiments, the compound has a methyl galacturonate to galacturonic acid ratio ranging from 2:1 to 1:2.

In some embodiments, the compound is a galactomannan (GM) polysaccharide composition produced as described in U.S. Patent Application US20110077217, incorporated expressly by reference in its entirety for all purposes.

In some embodiments, the average molecular weight of the GM compound is approximately 4,000 and 60,000 Da, as determined by the SEC-MALLS method.

In some embodiments, the compound is a modified synthetic disaccharide (MSD) produced as described in U.S. Pat. Nos. 6,444,655, 7,230,096, 7,638,623, 7,700,763, and 8,092,825, which are incorporated expressly by reference for all purposes.

In some embodiments, the compound is a peptide/protein inhibitor agent (PIA) that may bind to galectin and inhibit galectin function which may include, but not limited to, the PIA produced as described in U.S. Pat. No. 6,770,622, which is incorporated expressly by reference for all purposes.

In some embodiments, the compound is a peptidomimetic agent (PMA) that may bind to galectin and inhibit galectin function which may include, but not limited to, anginex and OTX-008 (also known as PTX-008) produced as described in U.S. Pat. No. 8,207,228, which is incorporated expressly by reference for all purposes.

In some embodiments, the compound is a galectin-specific monoclonal antibody (GSA).

In some embodiments, the compound is a small organic molecule (SOM) that interacts with various domains of galectin molecules that includes, but is not limited to, the carbohydrate binding domain and the protein dimerization domain.

In some embodiments, GRG and GA-RG bind to the galectin-3 molecule at multiple amino acid residues in the canonical carbohydrate recognition domain on the S-face of the b-sandwich binding domain as well as amino acid residues on the opposing F-face of the protein.

In some embodiments, the binding of GRG and GA-RG to the amino acid residues in the galectin-3 molecule are responsible for interfering with function of the galectin-3 molecule.

In some embodiments, modified synthetic disaccharides (MSD) bind to similar sites in the galectin-3 carbohydrate domain as GA-RG and can have similar function in inhibiting the function of the galectin-3 molecule.

In some embodiments, peptide/protein inhibitor agents (PIA) bind to similar sites in the galectin-3 carbohydrate domain as GA-RG and can have similar function in inhibiting the function of the galectin-3 molecule.

In some embodiments, peptidomimetic agents (PMA) bind to similar sites in the galectin-3 carbohydrate domain as GA-RG and can have similar function in inhibiting the function of the galectin-3 molecule.

In some embodiments, galectin-specific antibodies (GSA) bind to similar sites in the galectin-3 carbohydrate domain as GA-RG and can have similar function in inhibiting the function of the galectin-3 molecule.

In some embodiments, small organic molecules (SOM) bind to similar sites in the galectin-3 carbohydrate domain as GA-RG and can have similar function in inhibiting the function of the galectin-3 molecule.

In some embodiments, the GRG, GA-RG, GM, MSD, PIA, PMA, GSA, or SOM compounds described herein are used in combination with a therapeutically effective amount of monoclonal antibody that binds to CTLA-4 (anti-CTLA-4). CTLA-4 (Cytotoxic T-Lymphocyte Antigen 4), also known as CD152 (Cluster of differentiation 152), is a protein receptor that down-regulates the immune system and can be found on the surface of T cells, which lead the cellular immune attack on antigens.

In some embodiments, the GRG, GA-RG, GM, MSD, PIA, PMA, GSA, or SOM compounds described herein are used in combination with a therapeutically effective amount of monoclonal agonist antibody that binds to OX40 (anti-OX40) or recombinant OX40L that acts as agonist. OX40 is a member of the tumor necrosis factor/nerve growth factor receptor (TNFR/NGFR) family. OX40 may play a role in T-cell activation as well as regulation of differentiation, proliferation or apoptosis of normal and malignant lymphoid cells.

In some embodiments, the GRG, GA-RG, GM, MSD, PIA, PMA, GSA, or SOM compounds described herein are used in combination with a therapeutically effective amount of monoclonal antibody that binds to PD-1 (anti-PD-1). PD-1 refers to Programmed cell death protein 1 which is a member of the CD28/CTLA-4 family of T cell regulators.

In some embodiments the GRG, GA-RG, GM, MSD, PIA, PMA, GSA, or SOM compounds described herein can be used in combination with a therapeutically effective amount of monoclonal antibody, peptide or other agent that binds to lymphocyte co-stimulatory ligands or receptors and act as either antagonists or agonists of co-stimulation. Co-stimulatory receptors include, but are not limited to, CD28 and ICOS and ligands include, but are not limited, to CD80, CD86, and ICOS ligand.

In some embodiments, the GRG, GA-RG, GM, MSD, PIA, PMA, GSA, or SOM compounds described herein can be used in combination with a therapeutically effective amount of monoclonal antibody, peptide or other agent that binds to lymphocyte inhibitory ligands or receptors and act as either antagonists or agonists of lymphocyte inhibition. Inhibitory receptors include, but are not limited, to CTLA-4 and ligands include but are not limited to CD80 and CD86.

In some embodiments the GRG, GA-RG, GM, MSD, PIA, PMA, GSA, or SOM compounds described herein can be used in combination with a therapeutically effective amount of monoclonal antibody that binds to CTLA-4 (anti-CTLA-4).

In some embodiments the GRG, GA-RG, GM, MSD, PIA, PMA, GSA, or SOM compounds described herein can be used in combination with a therapeutically effective amount of monoclonal antibody, peptide or other agent that binds to the tumor necrosis factor receptor (TNFR) superfamily of receptors or their ligands which are expressed on lymphocytes and act as either antagonists or agonists of lymphocyte co-stimulation. Members of the TNFR superfamily of receptors include, but are not limited to, CD134, also known as OX40, 4-1BB (CD137), and CD27 and TNFR receptor ligands which include but are not limited to OX40L, 4-1 BBL (CD137L) and CD70.

In some embodiments, the GRG, GA-RG, GM, MSD, PIA, PMA, GSA, or SOM compounds described herein can be used in combination with a therapeutically effective amount of monoclonal antibody that binds to OX40 (anti-OX40), the GA-RG or GM compounds described herein can be used in combination with a therapeutically effective amount of recombinant OX40L or other agonists of OX40.

In some embodiments, the GRG, GA-RG, GM, MSD, PIA, PMA, GSA, or SOM compounds described herein can be used in combination with a therapeutically effective amount of monoclonal antibody that binds to PD-ligands (anti-PD-L1 and PD-L2).

In some embodiments, the GRG, GA-RG, GM, MSD, PIA, PMA, GSA, or SOM compounds described herein can be used in combination with a therapeutically effective amount of monoclonal antibody that binds to PD-1 (anti-PD-1).

In some embodiments, the GRG, GA-RG, GM, MSD, PIA, PMA, GSA, or SOM compounds described herein can be used in combination with a therapeutically effective amount of monoclonal antibody, peptide or other agent that modifies activation or function of dendritic cells thereby altering antigen processing or response.

In some embodiments, the GRG, GA-RG, GM, MSD, PIA, PMA, GSA, or SOM compounds described herein can be used in combination with a therapeutically effective amount of a tumor-antigen directed vaccine or a cancer vaccine. In some embodiments, the GRG, GA-RG, GM, MSD, PIA, PMA, GSA, or SOM compounds described herein can be used in combination with adjuvants. Adjuvants, in some embodiments, may include TLR ligands such as polyI:C, CpG, and the like.

In some embodiments, the GRG, GA-RG, GM, MSD, PIA, PMA, GSA, or SOM compounds described herein can be used in alone in combination with a therapeutically effective amount of a tumor-antigen directed vaccine or a cancer vaccine.

In some embodiments, the GRG, GA-RG, GM, MSD, PIA, PMA, GSA, or SOM compounds described herein can be used in combination with a therapeutically effective amount of a vaccine used for the purpose of treating or preventing an infectious disease.

In some embodiments, the GRG, GA-RG, GM, MSD, PIA, PMA, GSA, or SOM compounds described herein can be used in alone in combination with a therapeutically effective amount of any of the foregoing agents or combination or any of the foregoing agents.

An effective intra-peritoneal or intravenous dose of the GRG or GA-RG polysaccharide used in combination with a therapeutically effective dose of anti-OX40, anti-CTLA4, anti-PD-1, or other immune modulatory agent, or combination of any of the foregoing, to an experimental animal (e.g. mouse) can be between 10 and 120 mg/mg given once a week, twice a week, or three times per week.

An effective intravenous or dose of GRG or GA-RG used in combination with a therapeutically effective dose of anti-OX40, anti-CTLA-4, anti-PD-1, or other immune modulatory agent or combination of any of the foregoing, to a human subject can be between 0.5 and 15 mg/kg given once weekly, twice a week, or three times per week, as calculated from equivalency from animal dose.

An effective dose of GRG or GA-RG used in combination with a therapeutically effective dose of anti-OX40, anti-CTLA-4, anti-PD-1, or other immune modulatory agent, or combination of any of the foregoing, to a human subject can be administered subcutaneously, by other parenteral routes, or orally in multiples of between 1 and 100 times the intravenous dose.

An effective intra-peritoneal or intravenous dose of GM compounds described herein used in combination with a therapeutically effective dose of anti-OX40, anti-CTLA-4, anti-PD-1, or other immune modulatory agent, or combination of any of the foregoing, to an experimental animal (e.g. mouse) can be between 10 and 180 mg/mg given once a week, twice a week, or three times per week.

An effective intravenous or dose of GM used in combination with a therapeutically effective dose of anti-OX40, anti-PD-1, or other immune modulatory agent or combination of any of the foregoing, to a human subject can be between 0.5 and 20 mg/kg given once weekly, twice a week, or three times per week, as calculated from equivalency from animal dose.

An effective dose of GM compound used in combination with a therapeutically effective dose of anti-OX40, anti-CTLA-4, anti-PD-1, or other immune modulatory agent or combination of any of the foregoing, to a human subject can be administered subcutaneously, by other parenteral routes, or orally in multiples of between 1 and 100 times the intravenous dose.

In some embodiments, the efficacy of the composition for parenteral administration is determined by at least a 10% increase in the proliferation of CD8+ or CD4+ T-cells. In some embodiments, the efficacy of the composition for parenteral administration is determined by at least a 15% increase in the proliferation of CD8+ or CD4+ T-cells. In some embodiments, the efficacy of the composition for parenteral administration is determined by at least a 20% increase in the proliferation of CD8+ or CD4+ T-cells.

In some embodiments, the efficacy of the composition for parenteral administration is determined by at least a 10% increase in the proliferation of CD8+ or CD4+ T-cells as measured by expression of Ki-67. In some embodiments, the efficacy of the composition for parenteral administration is determined by at least a 15% increase in the proliferation of CD8+ or CD4+ T-cells as measured by expression of Ki-67. In some embodiments, the efficacy of the composition for parenteral administration is determined by at least a 20% increase in the proliferation of CD8+ or CD4+ T-cells as measured by expression of Ki-67.

In some embodiments, the efficacy of the composition for parenteral administration is not associated with general proliferation of CD8+ or CD4+ T-cells.

In some embodiments, the efficacy of the composition for parenteral administration is determined by at least a 10% up to 25% increase in the activation of CD8+ T-cells or CD4+ T-cells. In some embodiments, the efficacy of the composition for parenteral administration is determined by at least a 15% increase up to 25% in the activation of CD8+ T-cells or CD4+ T-cells. In some embodiments, the efficacy of the composition for parenteral administration is determined by at least a 20% increase in the activation of CD8+ T-cells or CD4+ T-cells.

In some embodiments, the efficacy of the composition for parenteral administration is determined by at least a 10% increase in the activation of CD8+ T-cells or CD4+ T-cells as measured by expression of granzyme B. In some embodiments, the efficacy of the composition for parenteral administration is determined by at least a 15% increase in the activation of CD8+ T-cells or CD4+ T-cells as measured by expression of granzyme B. In some embodiments, the efficacy of the composition for parenteral administration is determined by at least a 20% increase in the activation of CD8+ T-cells or CD4+ T-cells as measured by expression of granzyme B.

In some embodiments, the efficacy of the composition for parenteral administration is not associated with general increase in granzyme B expression in CD8+ or CD4+ T-cells.

In some embodiments, the efficacy of the composition for parenteral administration is associated with an increase by at least 10% of tumor antigen-specific CD8+ or CD4+ T-cells. In some embodiments, the efficacy of the composition for parenteral administration is associated with an increase by at least 15% of tumor antigen-specific CD8+ or CD4+ T-cells. In some embodiments, the efficacy of the composition for parenteral administration is associated with an increase by at least 20% of tumor antigen-specific CD8+ or CD4+ T-cells.

In some embodiments, the efficacy of the composition for parenteral administration is associated with an increase by at least 10% of GR-1 negative/CD11b positive cells. In some embodiments, the efficacy of the composition for parenteral administration is associated with an increase by at least 15% of GR-1 negative/CD11b positive cells. In some embodiments, the efficacy of the composition for parenteral administration is associated with an increase by at least 20% of GR-1 negative/CD11b positive cells.

In some embodiments, the efficacy of the composition for parenteral administration is associated with a decrease by at least 10% of GR-1 intermediate or positive/CD11b positive cells. In some embodiments, the efficacy of the composition for parenteral administration is associated with a decrease by at least 15% of GR-1 intermediate or positive/CD11b positive cells. In some embodiments, the efficacy of the composition for parenteral administration is associated with a decrease by at least 20% of GR-1 intermediate or positive/CD11b positive cells.

In some embodiments, the efficacy of the composition for parenteral administration is associated with a decrease by at least 10% of the size of the tumor (as compared its size at the beginning of the treatment). In some embodiments, the efficacy of the composition for parenteral administration is associated with a decrease by at least 15% of the size of the tumor. In some embodiments, the efficacy of the composition for parenteral administration is associated with a decrease by at least 20% of the size of the tumor.

In some embodiments, the efficacy of the composition for parenteral administration is associated with a decrease by at least 10% of the size or number of distant metastases from the primary tumor. In some embodiments, the efficacy of the composition for parenteral administration is associated with a decrease by at least 15% of the size or number of distant metastases from the primary tumor. In some embodiments, the efficacy of the composition for parenteral administration is associated with a decrease by at least 20% of the size or number of distant metastases from the primary tumor.

in some embodiments, the sum total of the volume occupied by all of the lesions may be represented in terms of a single number called "Total Tumor Burden" (TTB). As such, when any of the tumors respond to a chosen treatment plan, the TTB will change. In some embodiments, the TTB can be determined in a subject after treatment with the combination therapy comprising the compound described herein (e.g. carbohydrate compound) in combination with an immune modulatory agent and compared to the TTB of a subject treated with the immune modulatory agent alone. Yet, in other embodiments, the TTB can be determined in a subject after treatment with the compound described (e.g. carbohydrate compound) herein and compared to the TTB of a subject treated with a standard therapy (e.g. approved agent for the treatment of a cancer).

In some embodiments, tumors treated with the carbohydrate compound (e.g. GA-RG) alone or in combination with other immunotherapies (e.g. immune modulatory agents) may be evaluated using the immune-related response criteria in solid tumors. In some embodiments, the immune-related response criteria used can be the criteria described by Hoos et al. (J Natl Cancer Inst. 102:1388-1397 and Clinical Cancer research 15:74, 2009), which is hereby incorporated herein by reference in its entirety. Tumor measurability can be defined as 5×5 mm or more on helical computer tomography scans. The sum of the perpendicular diameters (SPD) of index lesions at baseline can be added to that of new lesions to calculate total tumor burden (TTB) according to the following formula: Total Tumor Burden=SPD of index lesions+SPD new measurable lesions.

In some embodiments, change in tumor burden can be assessed relative to the baseline tumor burden, that is, SPD of all index lesions at baseline. If there is a 100% reduction of index and new measurable tumor burden to baseline tumor burden the overall response is irCR (immune-related response Complete Response). If there is a greater than or equal to 50% reduction of index and new measurable tumor burden to baseline tumor burden the overall response is irPR (immune-related response Partial Response). If there is a less than 50% decrease to less than 25% increase in the index and new measurable tumor burden to baseline tumor burden the overall response is irSD (immune-related response Stable Disease). If there is a greater than or equal to 25% increase in the index and new measurable tumor burden to baseline tumor burden the overall response is irPD (immune-related response Progressive Disease), assuming that the response and progression are confirmed by a second assessment at least 4 weeks apart.

In some embodiments, the efficacy of the composition for parenteral administration is directly related to the level of expression of galectin-3 in the tumor with increased efficacy associated with increased galectin-3 expression in the tumor.

In some embodiments, the efficacy of the composition for parenteral administration in cancer therapy may be directly related to the level of expression of galectin-3 in the tumor cells and galectin-3 secreted into the tumor microenvironment with increased galectin-3 levels related to better efficacy.

In some embodiments, the efficacy of the composition for parenteral administration may be used in therapy of multiple cancer including but not limited to gastrointestinal cancers (esophageal, stomach, small intestine, colon, and anal), pancreatic cancer (endocrine and adenocarcinoma), bile duct cancer, liver cancers of various types, sarcomas, myosarcomas, breast cancer, lung cancer, head and neck cancer, mouth cancer, skin cancer, melanoma, kidney cancer, urinary and bladder, prostate cancer, testicular cancer, ovarian cancer, endometrial cancer, neurological cancers (brain and nerves), endocrine gland cancer (thyroid, adrenal, parathyroid, pituitary), bone cancer (osteosarcoma), hematological cancers (lymphoma, leukemia), multiple myeloma, and myelofibrosis.

In some embodiments, the method of treating further comprises the steps of administering to a subject an effective dose of the composition for parenteral administration or in combination with an immunomodulatory antibody or that results in at least one of the following:

at least a 10% increase in evidence of activation in circulating CD8+ or CD4+ T-cells as indicated by a variety of methods including but not limited to Ki-67 and/or granzyme B expression.

at least a 10% increase in tumor antigen-specific CD8+ or CD4+ T-cells.

at least a 10% response rate in tumor size or progression, progression free survival (patient survival without progression of the cancer) or an overall increase in patient survival.

at least a 10% reduction in the size or number of metastases distant from the primary tumor.

a statistically significant difference in Total Tumor Burden as assessed by the immune-related response criteria when compared to standard therapy alone, no therapy or therapy comprising the immune modulatory agent alone.

EXAMPLE 1: Enhancement of Immune and Prostate Tumor Response Following Co-Treatment with Anti-CTLA-4, Anti-OX40, or Anti-PD-1 in Combination with GA-RG and GM In this example, experiments were performed in a syngeneic model of mouse cancer. The tumor cells used were the TRAMP-C1 cell line which was derived from a mouse prostate cancer. To derive these cells, the SV40 large T antigen was expressed in a transgenic mouse with a prostate specific gene promoter, thereby expressing SV40 large T specifically in prostate tissue. The TRAMP-C1 cell line was derived from resultant prostate tumors; importantly, the cell line does not express SV40 large T-antigen. For the tumor model, TRAMP-C1 cells (1×10sup6 cells) were inoculated into normal C57BL/6 mice via subcutaneous injection.

Following inoculation with TRAMP-C1 cells, groups of mice were treated via intra-peritoneal injection with either IgG (as a control, on days 4, 6 and 8 days after inoculation), or anti-CTLA-4 (200 micrograms on days 4, 6 and 8 after inoculation), or anti-PD-1 (200 micrograms on days 4, 6 and 8 after inoculation), or anti-OX40 (250 micrograms on days 4 and 8 after inoculation).

Other groups of animal were treated with the same compounds as above plus either GA-RG or GM as described as follows: GA-RG, 2.4 mg/dose on days 4, 6, and 8, or GM, 2.4 mg/dose on days 4, 6, and 8 followed by GA-RG 28, 30, and 32.

FIG. 1 shows the results of experiments for the different groups of experimental animals (5 mice per group). The measurement, represented on the y axis is the percent of isolated CD8+ cells that are also positive for granzyme B. The protein granzyme B is a marker for effector function of CD8 positive lymphocytes. Granzymes are serine proteases that are released by cytoplasmic granules within CD8+ cytotoxic T-cells which are capable of inducing apoptosis in target cells such as tumor cells or virus infected cells. Comparison of rat IgG alone (control) to those animals treated with anti-OX40 (aOX40), anti-CTLA-4 (aCTLA-4), or anti-PD-1 (aPD-1) shows that the antibody control treatment resulted in a statistically non-significant increase in the percent of CD8+ cells expressing granzyme B.

FIG. 1 also shows the results of the addition of GM treatment to the treatment with aOX40, aCTLA-4, or aPD-1. Although there appears to be some activation of CD8+ cells when GM is added to therapy with IgG alone, these changes were not significant and there is no further augmentation of granzyme B positive cells when GM was added to treatment with aOX40, aCTLA-4, or aPD-1.

In contrast, the addition of GA-RG treatment to the treatment with aOX40, aCTLA-4, or aPD-1 showed a striking increase in activation of CD8+ cells. Addition of GA-RG to treatment with aOX40, aCTLA-4, or aPD-1 increased the percent of granzyme B positive CD8+ cells by 2-fold, 5-fold and 4-fold, respectively. This represents a highly significant and striking increase in the activation of CD8+ cells when GA-RG is added to the treatment.

Figure 2:
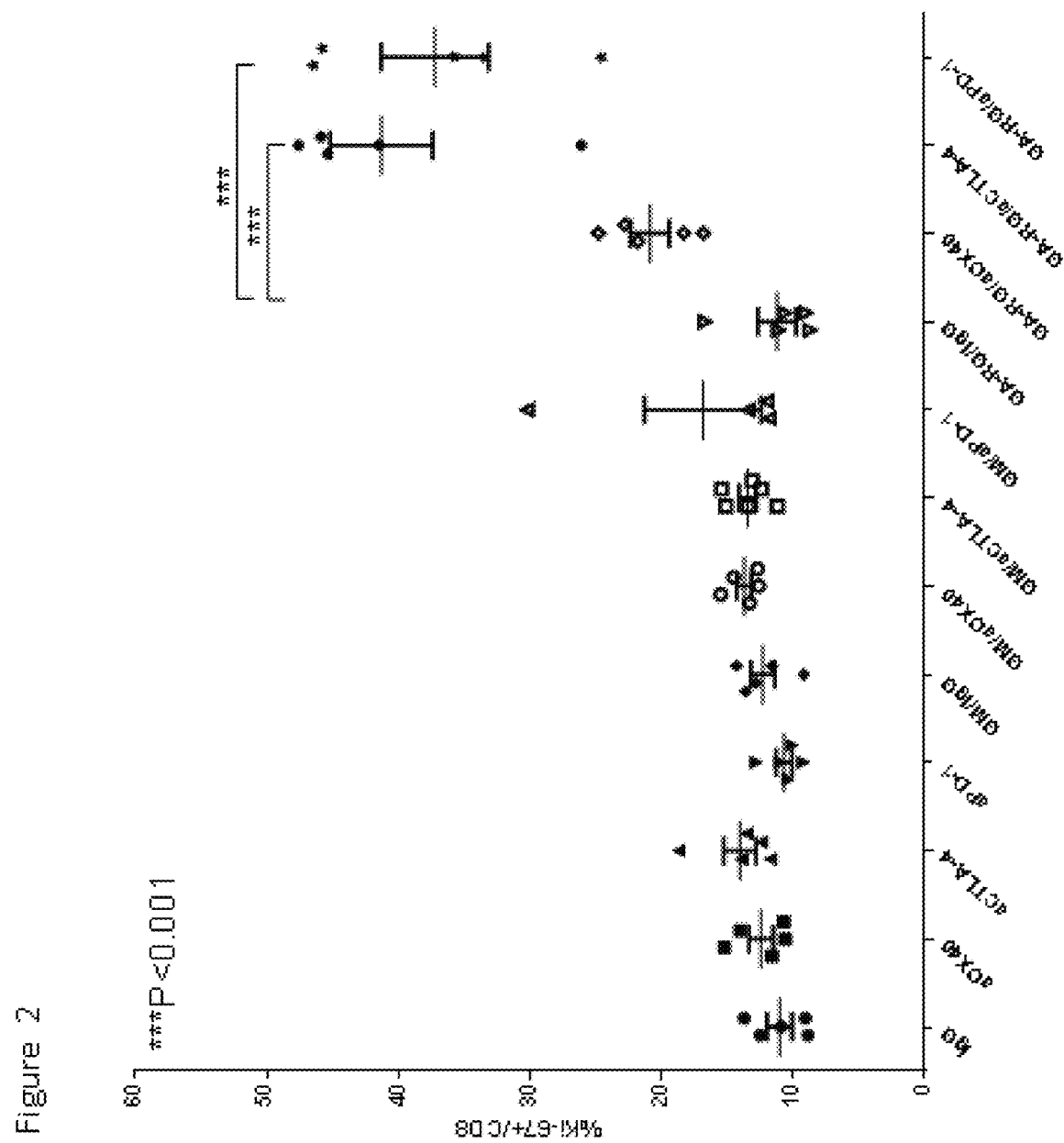
FIG. 2 depicts the percentage of peripheral blood lymphocytes from different experimental groups analyzed for the percent of CD8+ cells that express Ki-67.

FIG. 2 shows the results of a proliferation marker in CD8+ T cells for the different groups of experimental animals. The proliferation marker is Ki-67 which is a nuclear protein that is associated with cellular proliferation. There is little change in the proliferation of CD8+ cells after treatment with aOX40, aCTLA-4, or aPD-1 alone or in combination with GM. However, Ki-67 was markedly elevated with aOX40, aCTLA-4, or aPD-1 co-administered with GA-RG to very similar extents as the percent of granzyme B expression seen in FIG. 1.

Figure 3:
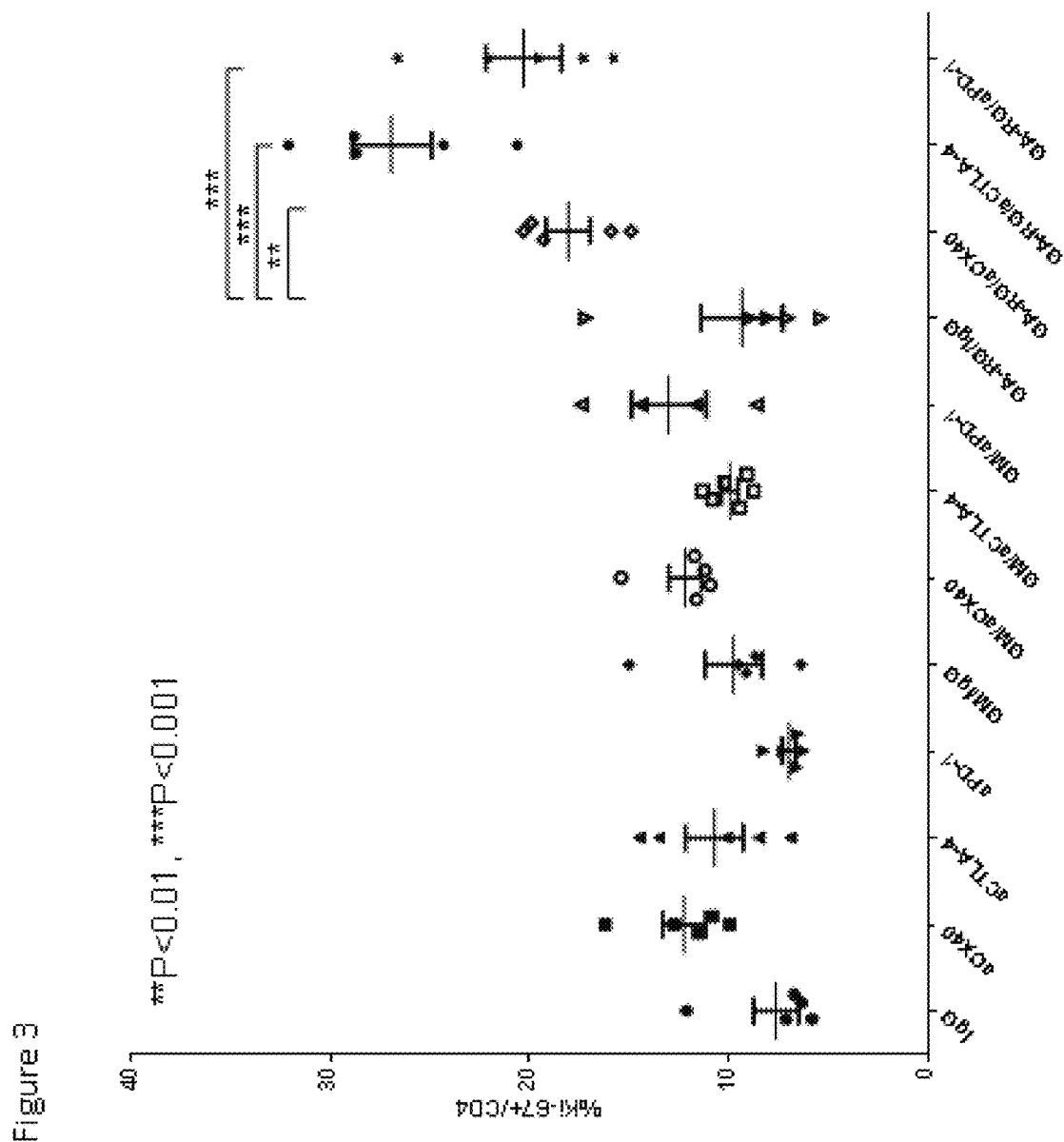
FIG. 3 depicts the percentage of peripheral blood lymphocytes from different experimental groups analyzed for the percent of CD4+ cells that express Ki-67.

FIG. 3 shows the results of the proliferation marker Ki-67 in CD4+ T cells for the different groups of experimental animals. There is little change in the proliferation of CD4+ cells after treatment with aOX40, aCTLA-4, or aPD-1 alone or in combination with GM. However, Ki-67 was markedly elevated with aOX40, aCTLA-4, or aPD-1 co-administered with GA-RG to very similar extents as seen in CD8+ cells (FIG. 2).

Figure 4:
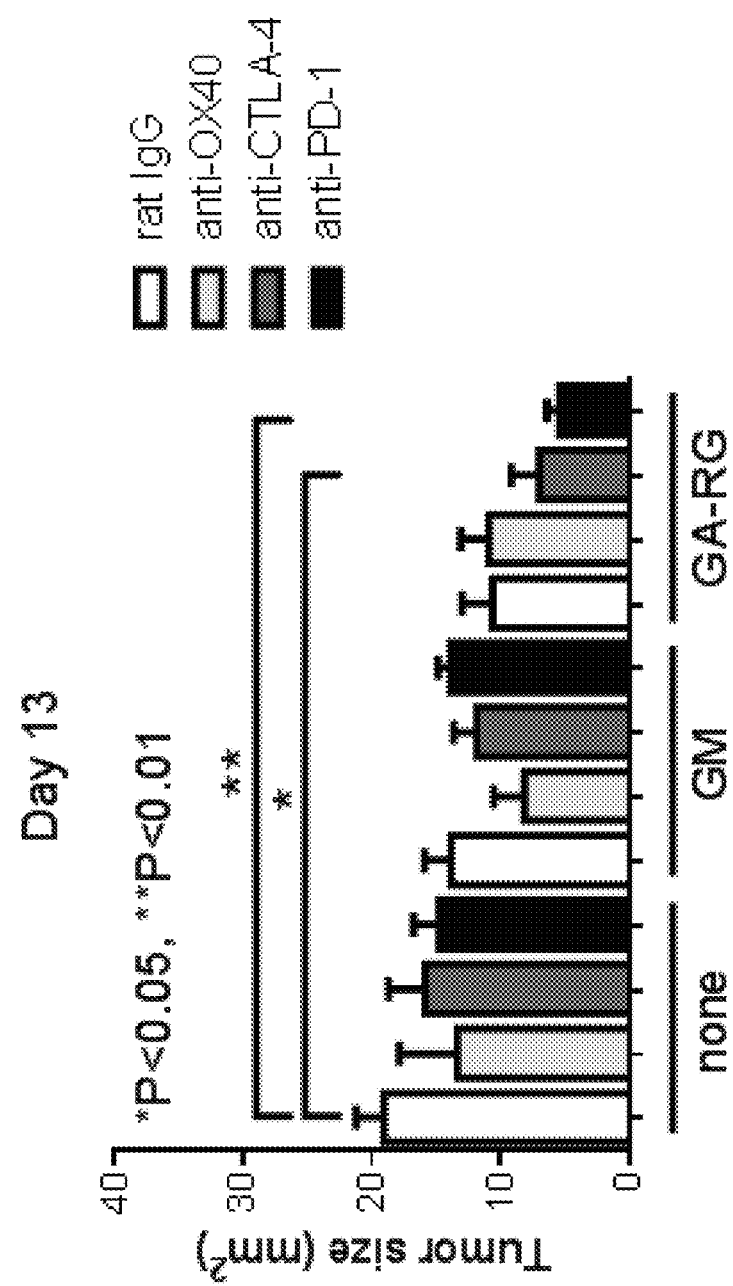
FIG. 4 depicts the size of TRAMP-C1 prostate tumors in mice at day 13 in the different experimental groups.

FIG. 4 shows the results of tumor growth in the different experimental groups. When GA-RG treatment was added to treatment with aCTLA4 or aPD-1 there was a significant reduction of tumor growth compared to therapy with the antibodies alone.

The results of these experiments demonstrate that when mice are treated with aOX40, aCTLA-4, or aPD-1 in combination with GA-RG there is a marked increase in the proliferation and activation of CD8+ cytotoxic T-cells, an increase in proliferation of CD4+ T regulatory cells, and a decrease in tumor size.

EXAMPLE 2: Enhancement of Immune and Prostate Tumor Response Following Co-Treatment with Anti-CTLA4 or Anti-OX40 in Combination with GA-RG In this example, experiments were performed in a syngeneic model of mouse cancer. The tumor cells used were the TRAMP-C1 cell line which was derived from a mouse prostate cancer, as described in Example 1.

The example includes six treatment groups of tumor inoculated mice with two groups in each of the following: IgG treated control mice with and without GA-RG (1.2 mg/dose) on days 4, 8, 11 and 15 after inoculation; mice treated with aOX40 (250 microgram or mcg) with and without GA-RG (1.2 mg/dose) on days 4, 8, 11 and 15 after inoculation; and mice treated with aCTLA4 (200 mcg) on days 4, 6, 8, 11, 13, and 15 after inoculation with and without GA-RG (1.2 mg/dose) on days 4, 8, 11 and 15 after inoculation.

Figure 5:
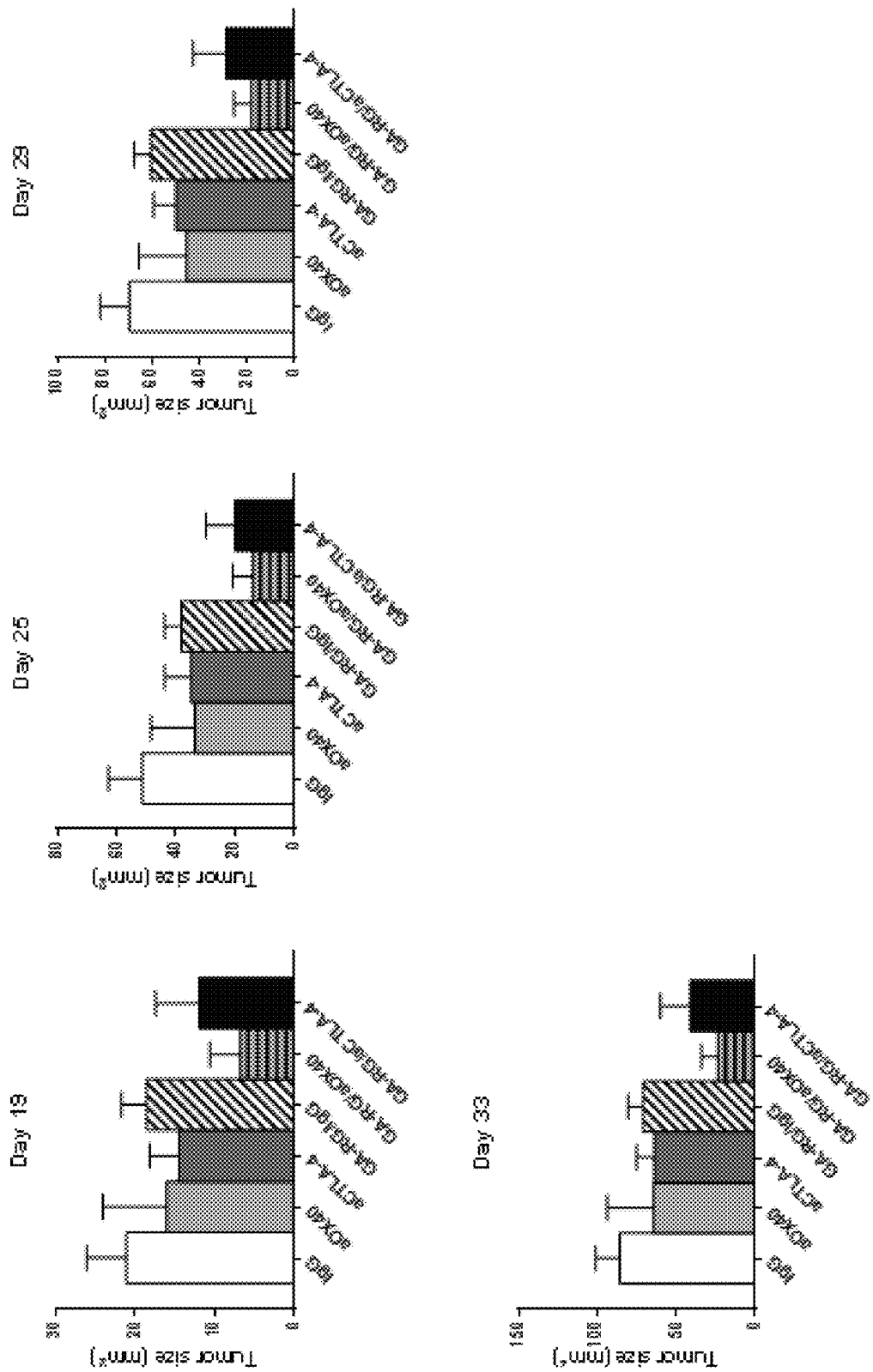
FIG. 5 depicts the size of TRAMP-C1 prostate tumors in mice at days 19, 25, 29, and 33 for the different experimental groups.

FIG. 5 shows results of these treatments on tumor size at various times after inoculation. While treatment with aOX40, aCTLA4, and GA-RG alone had minimal effect on the size of tumors, the combinations of aOX40 and aCTLA4 with GA-RG had a much greater effect in decreasing the tumor size at each time point out to day 33 after tumor inoculation.

Figure 6:
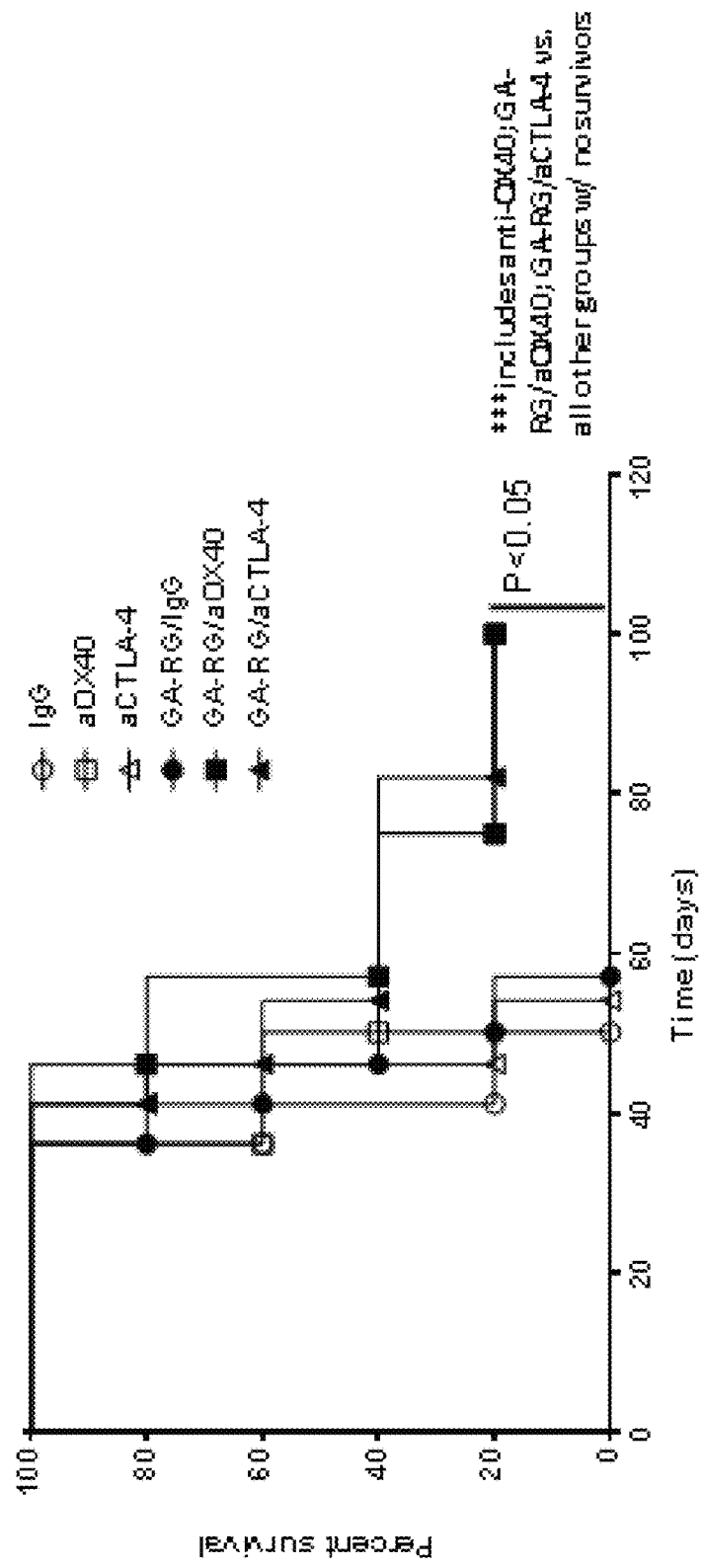
FIG. 6 depicts survival curves for the different experimental groups with TRAMP-C1 prostate cancer.

FIG. 6 shows the survival curves for the mice in the six treatment groups. The groups treated with combination of aOX40 and aCTLA4 with GA-RG had a doubling of survival.

The results of these experiments demonstrate that when mice were treated with aOX40 or aCTLA-4 in combination with GA-RG there was significantly more shrinkage of prostate tumors than with the drugs alone and an increase in survival. Twenty percent of mice treated with the combination of aOX40 or aCTLA4 had survivals over 100 days whereas all mice treated with either drug alone were dead by 58 days.

EXAMPLE 3: Enhancement of Immune and Breast Tumor Response Following Co-Treatment with Anti-CTLA4 or Anti-OX40 in Combination with GA-RG In this example, experiments were performed in a syngeneic model of mouse breast cancer. The tumor cells used were the 4T1 which is a syngeneic breast cancer cell line derived from a spontaneously arising BALB/c mammary tumor. When introduced orthotopically, the 4T1 line grows rapidly at the primary site and forms metastases in lungs, liver, bone and brain over a period of 3-6 weeks. When introduced via the tail vein or arterially, metastases are apparent in these same organs after 1-2 weeks. The rapid and efficient metastasis to organs affected in human breast cancer makes the 4T1 model an excellent mouse model for the study of metastatic progression of breast cancer in humans. Because the model is syngeneic in BALB/c mice, it can be used to study the role of the immune system in tumor growth and metastasis. For the tumor model in these experiments, 4T1 cells (5×10sup4 cells) were inoculated into normal C57BL/6 mice via subcutaneous injection.

The example includes six treatment groups of tumor inoculated mice with two groups in each of the following: IgG treated control mice with and without GA-RG (1.2 mg/dose) on days 4, 8, 11 and 15 after inoculation; mice treated with aOX40 (250 mcg) with and without GA-RG (1.2 mg/dose) on days 4, 8, 11 and 15 after inoculation; and mice treated with aCTLA4 (200 mcg) on days 4, 6, 8, 11, 13, and 15 after inoculation with and without GA-RG (1.2 mg/dose) on days 4, 8, 11 and 15 after inoculation.

Figure 7:
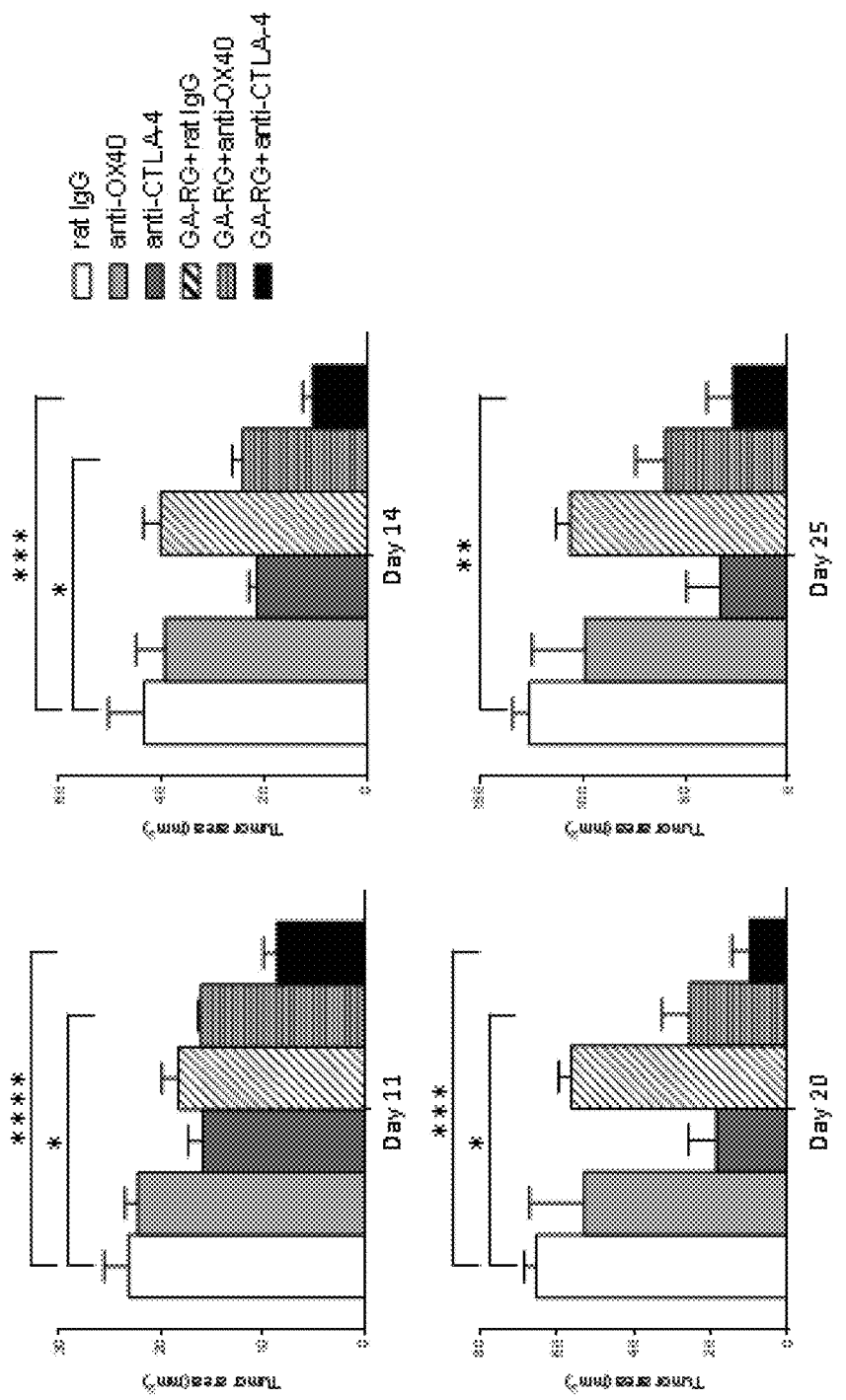
FIG. 7 depicts the size of breast tumors in mice at days 11, 14, 20, and 25 for the different experimental groups.

FIG. 7 shows results of these treatments on tumor size at various times after inoculation. While treatment with aOX40, aCTLA4, and GA-RG alone had some effect on the size of tumors, the combinations of aOX40 and aCTLA4 with GA-RG had a much greater effect in decreasing the tumor size at each time point out to day 25 after tumor inoculation.

The results of these experiments demonstrate that when mice are treated with aOX40 or aCTLA-4 in combination with GA-RG there is significantly more shrinkage of breast tumors than with the drugs alone and an increase in survival.

EXAMPLE 4: Enhancement of Survival and Reduction in Lung Metastasis Following Co-Treatment with Anti-OX40 in Combination with GA-RG In this example, experiments were performed in a syngeneic model of mouse breast cancer using 4T1 cells.

The example includes four treatment groups of tumor inoculated mice with two groups in each of the following: IgG treated control mice with and without GA-RG (2.4 mg/dose) on days 4, 8, 11 and 15 after inoculation; and mice treated with aOX40 (250 mcg) with and without GA-RG (2.4 mg/dose) on days 4, 8, 11 and 15 after inoculation.

As shown in FIG. 8A, the mice treated with the combination of aOX40 and GA-RG had a greater survival than mice treated with aOX-40 alone.

The number of lung metastases was evaluated in the animals using a clonagenic assay which evaluates the number of independent cell clones that grow out of homogenized lung. As shown in FIG. 8B, there was a 10 fold reduction in the number of lung metastases in the mice treated with the combination of aOX40 and GA-RG than mice treated with aOX-40 alone.

These results show that mice treated with the combination of aOX40 and GA-RG had a greater survival than mice treated with aOX-40 alone and that this effect may be related in part to a reduction in metastatic disease.

EXAMPLE 5: Alteration of Monocyte Populations

In this example, experiments were performed in a syngeneic model of mouse breast cancer using 4T-1 cells.

The example includes four treatment groups of tumor inoculated mice with two groups in each of the following: IgG treated control mice with and without GA-RG (2.4 mg/dose) on days 4, 8, 11 and 15 after inoculation; and mice treated with aOX40 (250 mcg) with and without GA-RG (2.4 mg/dose) on days 4, 8, 11 and 15 after inoculation.

Figure 9:
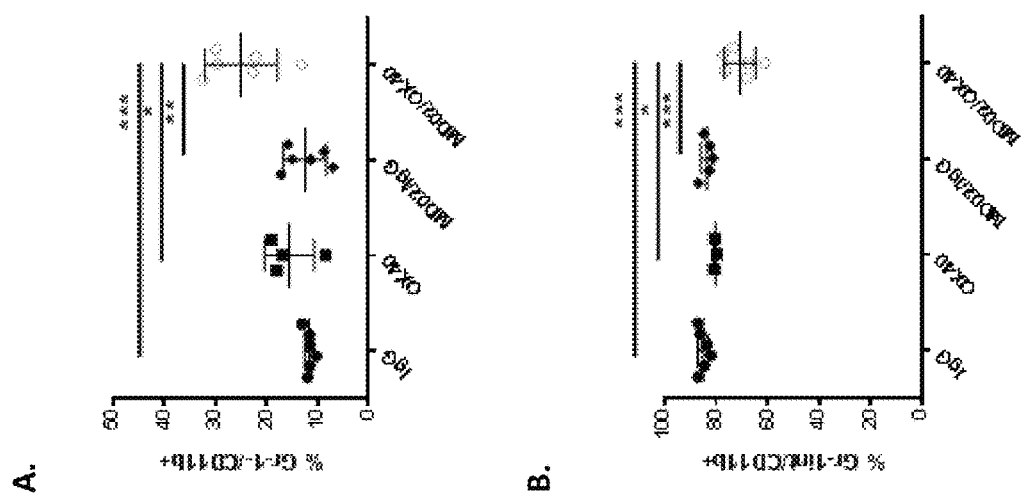
FIG. 9A depicts the percentage of GR-1 negative/CD11b positive cells in the circulation of 4T1 breast tumor bearing mice treated with aOX40 alone or in combination with GA-RG (labeled as MD02).
FIG. 9B depicts the percentage of GR-1 intermediate/CD11b positive cells in the circulation of 4T1 mammary carcinoma tumor bearing mice treated with aOX40 alone or in combination with GA-RG (labeled as MD02 in these figures). *$p<0.05$; $p<0.01$; *$p<0.001$.

As shown in FIG. 9A, the percentage of GR-1 negative/CD11b positive cells was increased in the circulation of animals treated with the combination of aOX-40 and GA-RG (labeled as MD02 in this graph)

In contrast, the number of GR-1 intermediate/CD11b positive cells was reciprocally reduced in animals treated with the combination of aOX40 and GA-RG (labeled as MD02 in this graph).

The elevation in GR-1 neg/CD11b positive cells is an indication of an increase in non-suppressor type mononuclear cells which is associated with less immune cell suppression that could be associated with a therapeutic effect on the tumor.

These results also suggest that the phenotype of mononuclear cells/macrophages may be altered in the circulation and tumor microenvironment in tumor bearing mice with the combination therapy.

EXAMPLE 6: Enhancement Efficacy in MCA205 Tumors, a Sarcoma Tumor Cell Line, Following Co-Treatment with Anti-OX40 in Combination with GA-RG In this example, experiments were performed in a syngeneic model of mouse sarcoma cancer using MCA205 cells.

The example includes four treatment groups of tumor inoculated mice with two groups in each of the following: IgG treated control mice (250 mcg; days 4, 8) with and without GA-RG (2.4 mg/dose) on days 4, 6, 8, 11, 13, and 15 after inoculation; and mice treated with aOX40 (250 mcg; days 4, 8) with and without GA-RG (2.4 mg/dose) on days 4, 6, 8, 11, 13, and 15 after inoculation.

Figure 10A:
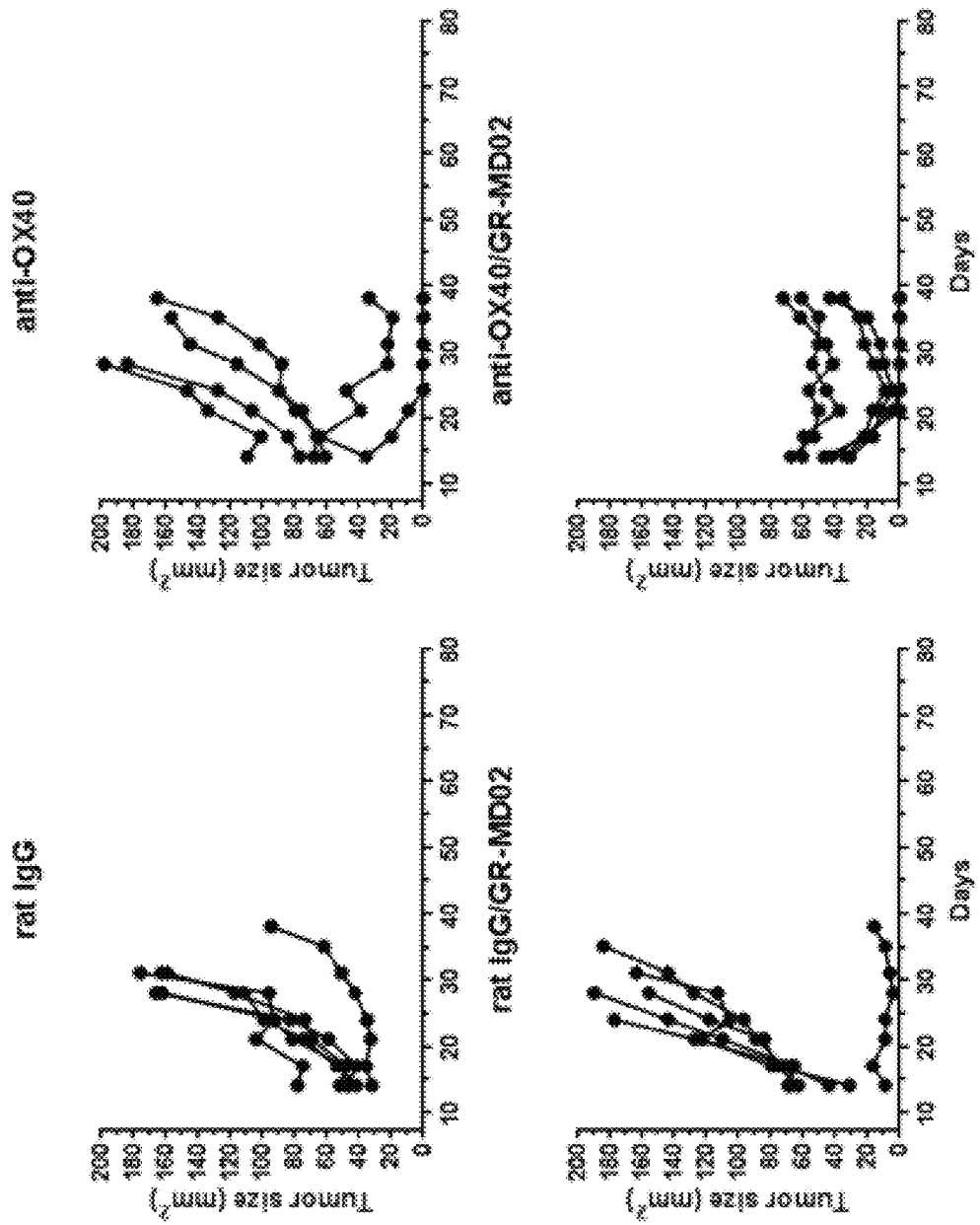
FIG. 10A shows the response of MCA-205 sarcoma tumor bearing mice to treatment with aOX40 alone or in combination with GA-RG (labeled as MD02 in these figures).

FIG. 10A shows a marked decrease in tumor size over time when aOX40 is administered in combination with GA-RG (labeled as GR-MD-02 in this figure) with very little tumor growth in the animals treated with the combination.

Figure 10B:
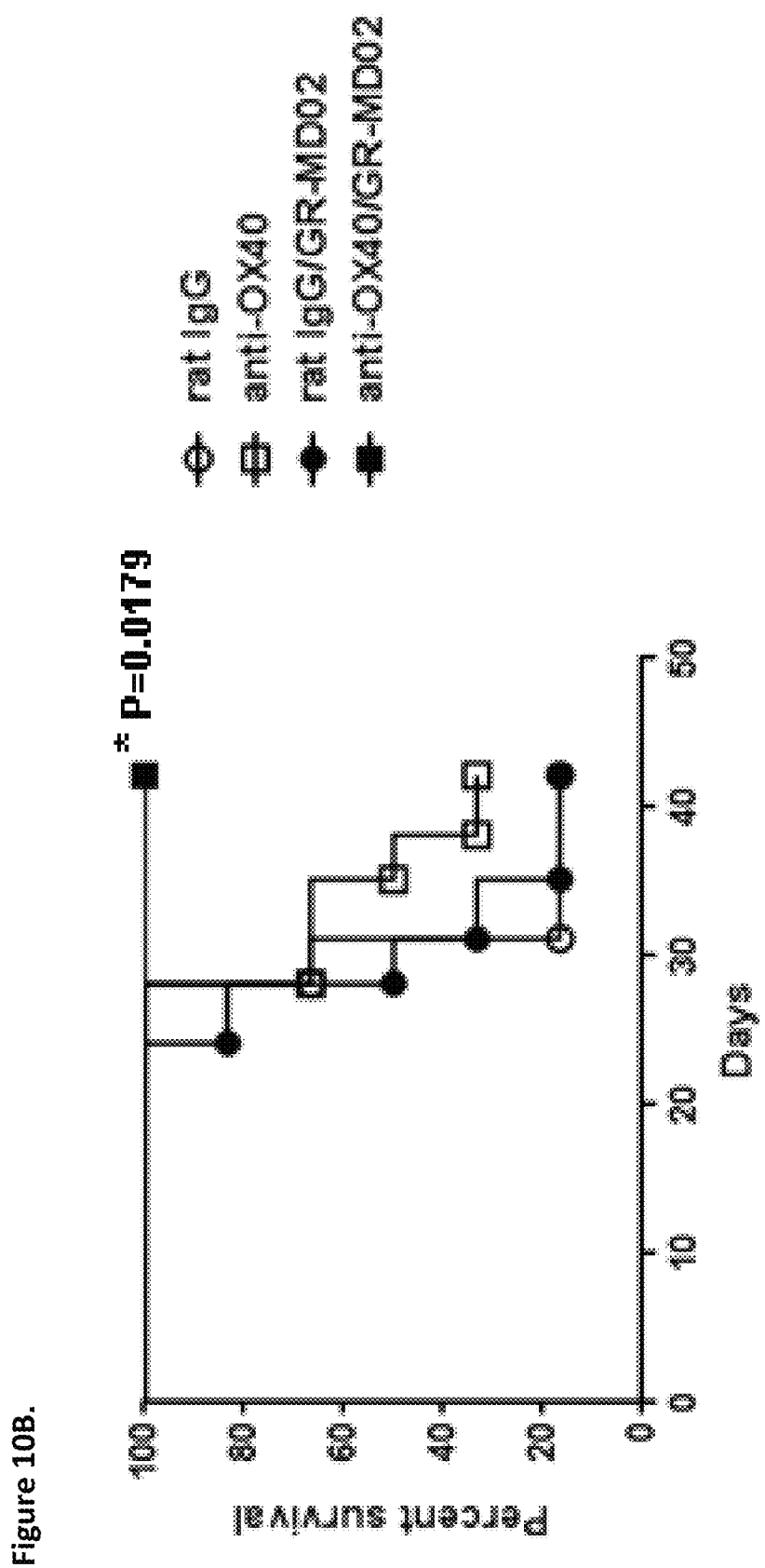
FIG. 10B shows the survival curves for the same animal groups.

FIG. 10B shows survival curves of the animals. There was a statistically significant improvement in survival in the animals who received aOX40 in combination with GA-RG (labeled as GR-MD-02 in this figure).

This demonstrates that a similar effect is seen with sarcoma tumor cells as with prostate and breast cancer cells, and in some aspects the effect is more robust than in those tumor models.

EXAMPLE 7: Expression of Galectin-3 in Tumor Cell Lines

The expression of galectin-3 was assessed in tumor cell lines used in these experiments, as well as other tumor cell lines.

Figure 11:
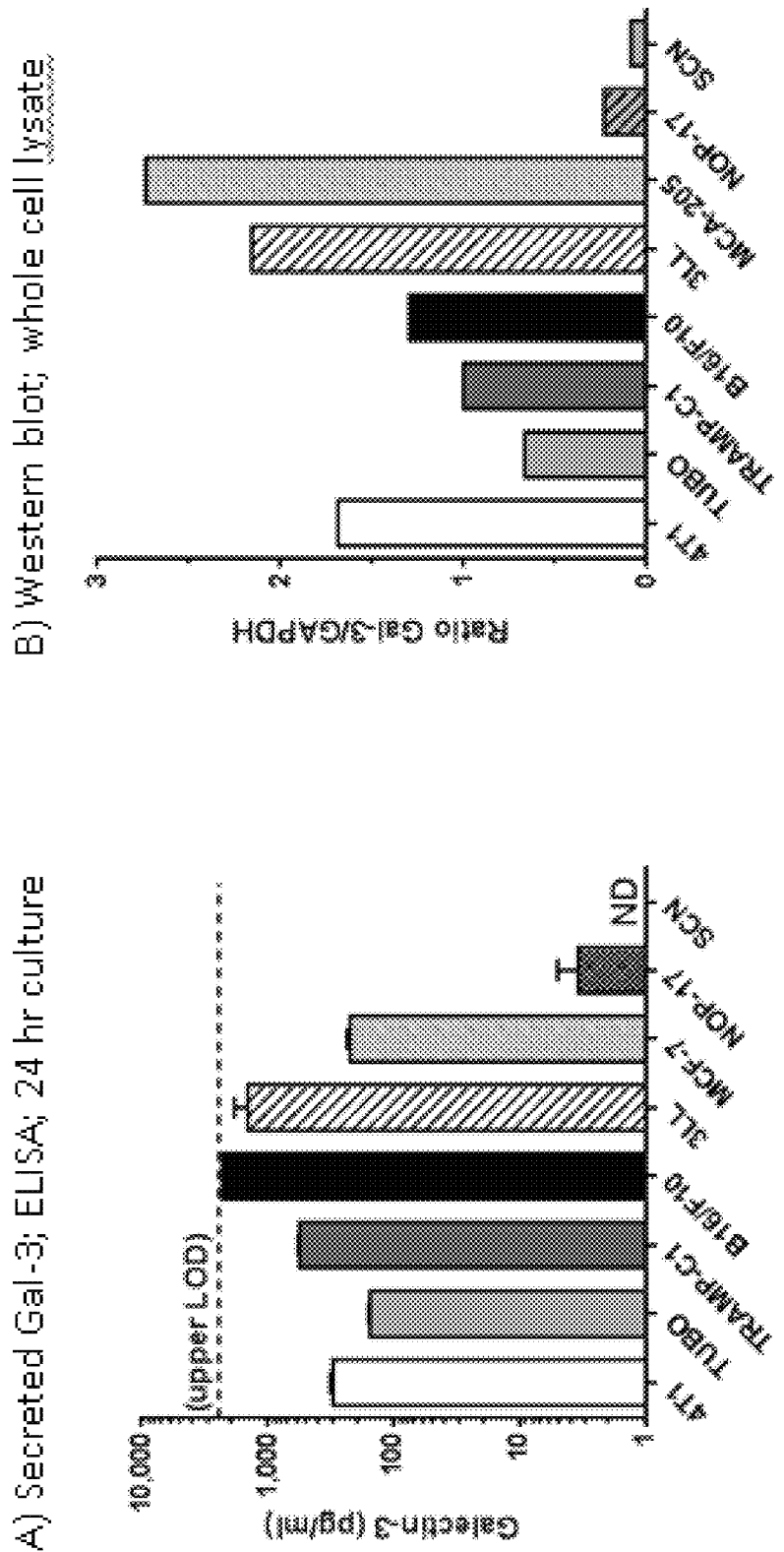
FIG. 11A depicts the expression of galectin-3 protein as secreted into media in various tumor cell lines.
FIG. 11B depicts the expression of galectin-3 protein in whole cell lysate in various tumor cell lines.

FIG. 11A shows that there were significant amounts of galectin-3 protein secreted into the culture media by multiple cell lines, with low or no secretion in NOP-17 and SCN cell lines. Importantly, two of the cell lines that were used in previous examples, 4T1 and TRAMP-C1, secreted large amounts of galectin-3. These data show that there are different levels of expression of galectin-3 in cell lines that may be related to drug efficacy.

FIG. 11B shows that there were significant amounts of galectin-3 protein in the whole cell lysates of multiple cell lines, with low amounts in NOP-17 and SCN cell lines. Importantly, three of the cell lines that were used in previous examples, 4T1, TRAMP-C1, and MCA-205, expressed large amounts of galectin-3.

Of note, the cell line that expressed the greatest amount of galectin-3, MCA-205 (FIG. 11B), was the most responsive to combination therapy with aOX40 and GA-RG (Example 6).

These results further suggest that the response of tumors to combination therapy with GA-RG is correlated with the level of expression of galectin-3.

EXAMPLE 8: Dual Role of Galectin-3 in T-Cell Activation

Immunosuppression and reduced cytolytic function of tumor infiltrating lymphocytes are major obstacles to creating effective therapies for patients. Galectin-3, a lectin family member, is expressed in numerous cancers including breast and prostate. Moreover, it is expressed ubiquitously by prostate epithelia, macrophages, and activated lymphocytes.

Endogenous galectin-3 promotes alternative macrophage activation and limits TCR-mediated CD4 T cell activation which limits antitumor immunity.

Since the regulatory effects of galectin-3 on inflammation and CD8 T cell function remain unknown, experiments were done to examine this issue.

It is hypothesized that galectin-3 within the tumor microenvironment promotes tumor progression by negatively regulating the function of CD8 T cells. To test this, the effects of endogenous galectin-3 deletion in CD8 T-cells were examined.

In vivo, antigen-specific Gal3−/− CD8 T-cells exhibited decreased effector function (decreased proliferation, granzyme B, IFN-gamma, and IL-2) compared to wild type (WT) controls.

Analysis of differential gene expression in antigen-specific Gal3−/− or Gal3+/+ CD8 T-cells found that granzyme B, CD25, KLRG-1, and Blimp-1 gene expression were reduced in Gal3−/− CD8 T cells as compared to controls.

In vitro studies demonstrated that antigen-specific Gal3−/− CD8 T cells had a significant reduction in CD25 and OX40 expression. These data suggest a novel and surprising finding, namely that galectin-3 has an important role in promoting CD8 T cell function, in contrast to its inhibitory role in CD4 function.

To assess the role for galectin 3 in the tumor microenvironment, galectin 3 expression was examined within the tumor using the TRAMP model of prostate carcinoma. Galectin 3 was expressed on macrophages and cancer cells within the tumor.

Galectin 3 inhibition with GA-RG (GR-MD-02) in vivo augmented CD8 T cell expansion and CD62L expression, suggesting dual roles for Gal3 in CD8 T cell function.

Figure 12:
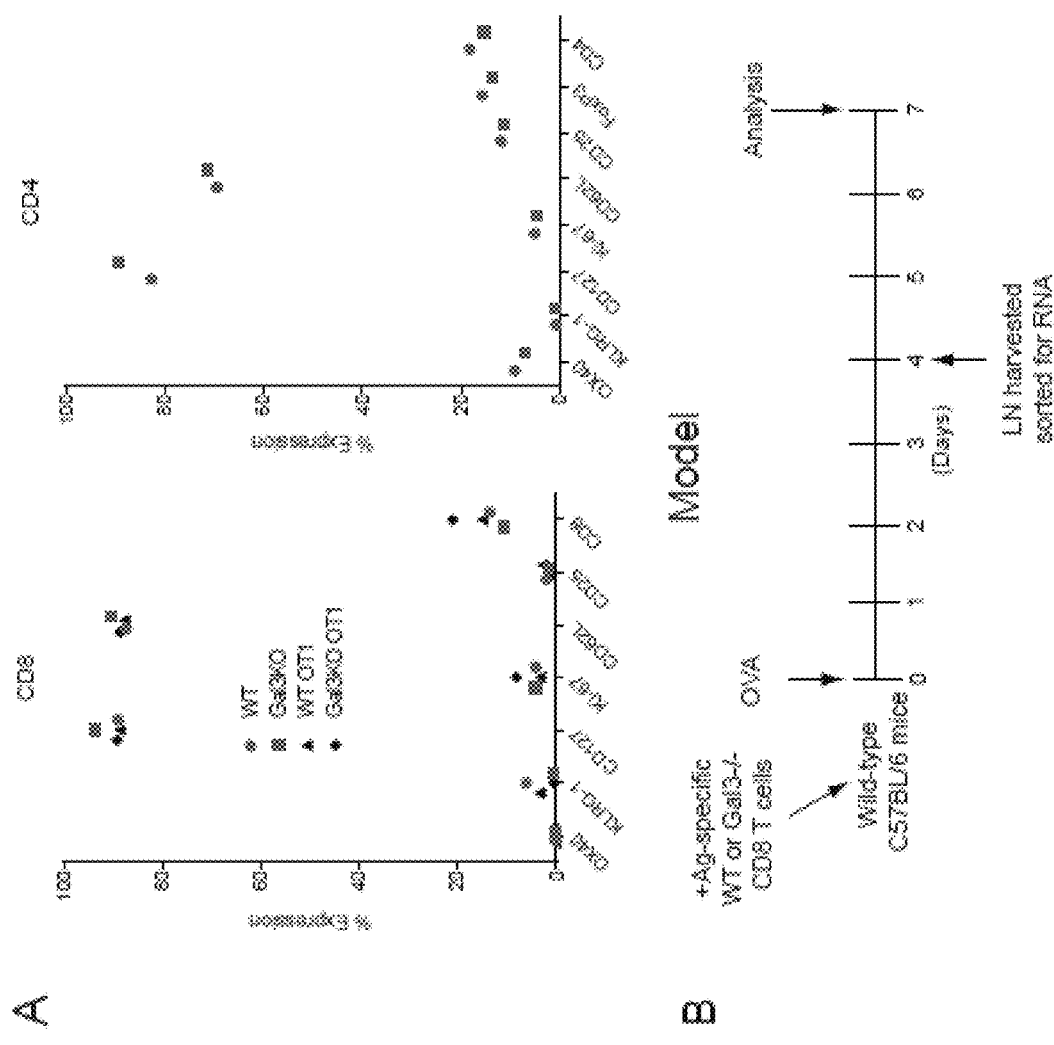
FIG. 12A depicts a phenotype comparison of naïve galectin-3 deficient CD8 T cells versus wild type CD8 T cells by flow cytometry analysis of various markers.
FIG. 12B is a schematic of the model used in the experiment.

FIG. 12 shows the phenotype comparison between naïve Galectin-3 deficient CD8 T cells and wild type (WT) CD8 T cells by flow cytometry. FIG. 12A shows the baseline expression of phenotypic markers on naive CD8 and CD4 in WT, Gal3−/−, WTOT-1, or Gal3−/− OT-1 mice was assessed on untreated splenocytes. For CD8 and CD4, the percent expression listed is the percent of live cells expressing either CD8 or CD4. FIG. 12B shows the model: Wild-type C57BL/6 mice received 3×10e6 naive WT or Gal3−/− OT-I CD8 T cells (iv) on day-1. Donor OT-I T cells were stimulated with 500 mcg soluble OVA (sq; d0).

Figure 13:
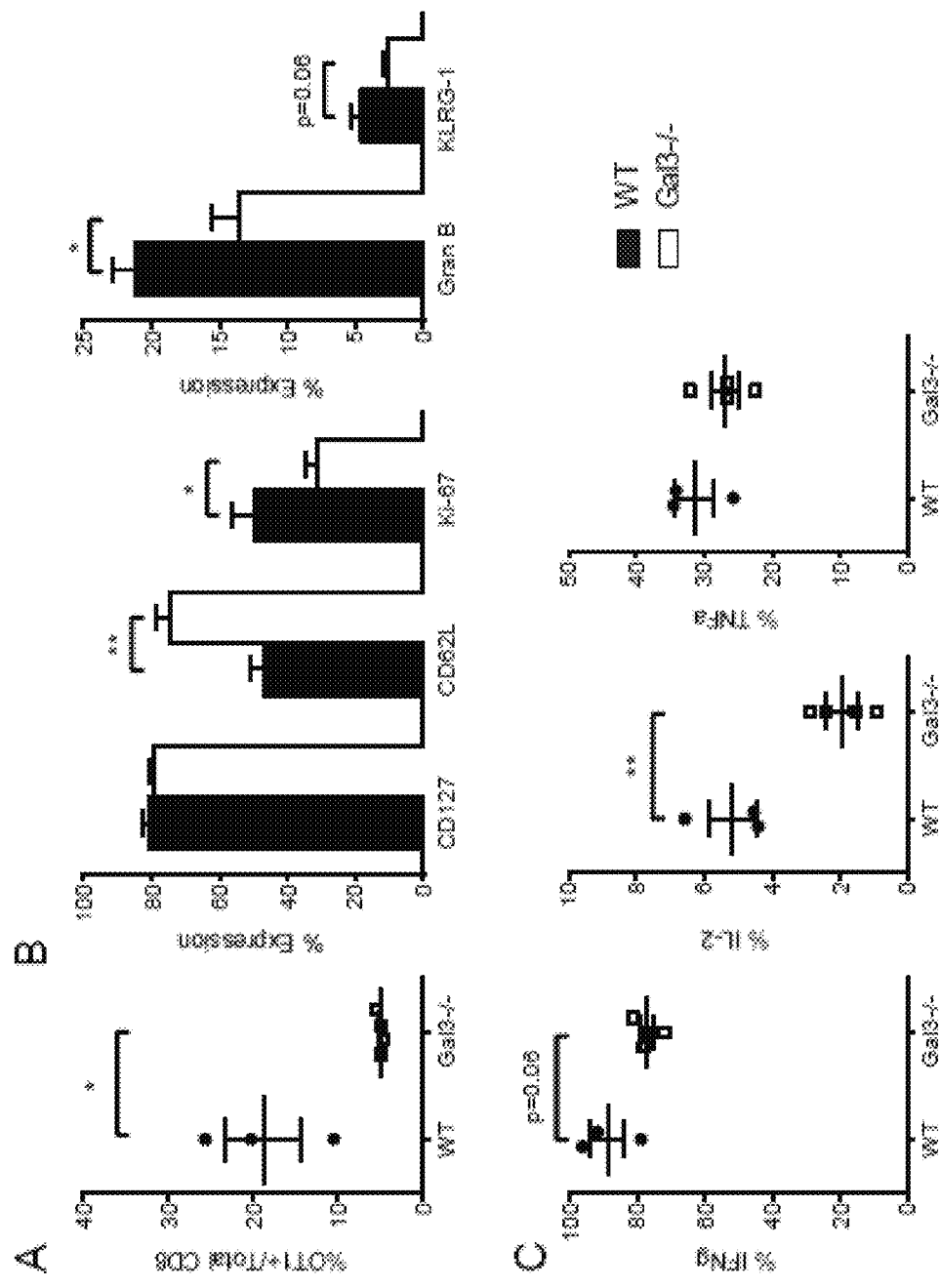
FIG. 13A-C depicts that galectin-3 deficient CD8 T cells exhibit reduced effector function following antigen stimulation in vivo.

FIG. 13 shows that galectin-3 deficient CD8 T cells exhibit reduced effector function following antigen stimulation in vivo. FIGS. 13A-C show the phenotype of donor OT-I T cells in the spleen which was determined by flow cytometry on day 7 post-stimulation. Graphs depict the mean from individual mice (n=4/group) from 1 of 3 independent experiments (*P<0.05; **P<0.01).

Figure 14:
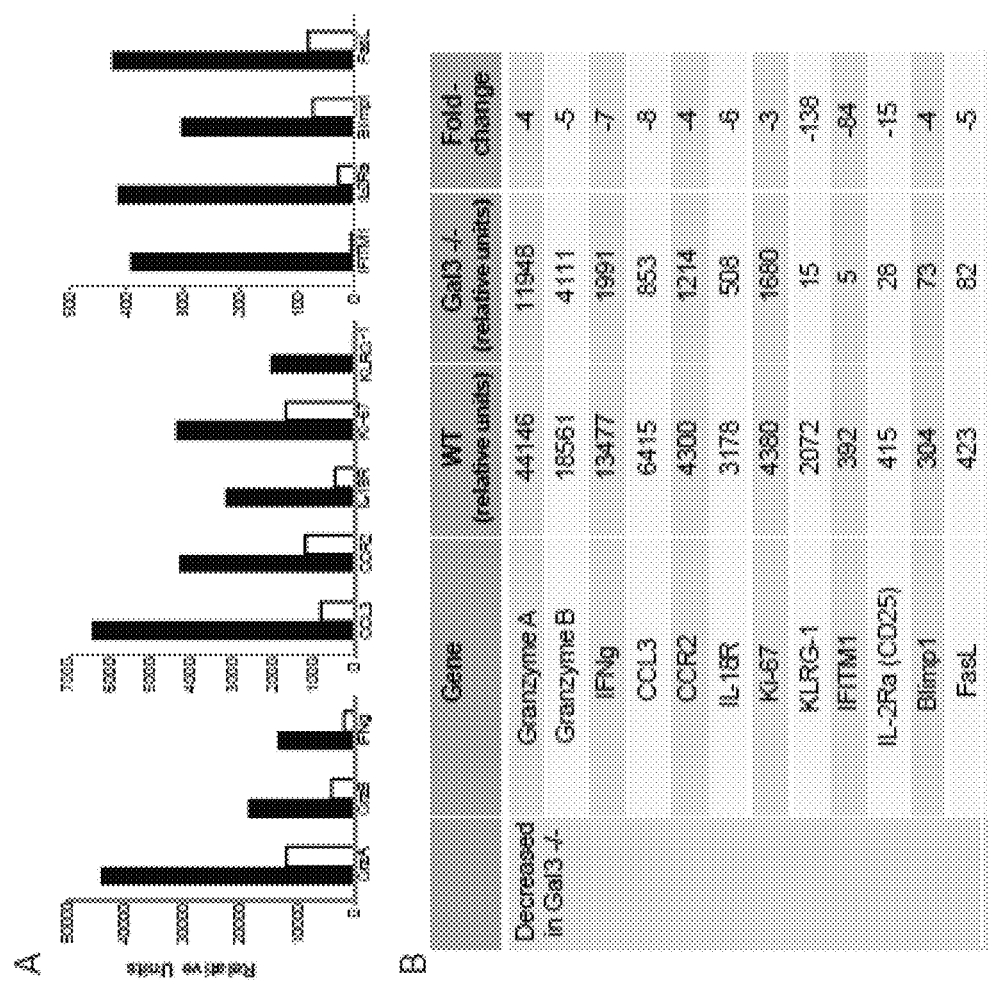
FIG. 14 depicts that selected genes are down-regulated in galectin-3 deficient CD8 T cells.

FIG. 14 shows that selected genes are down-regulated in Galectin-deficient CD8 T cells. Wild-type or Gal3−/− OT-1 T cells were adoptively transferred into wild-type hosts and then stimulated with OVA. Four days later, lymph nodes were harvested and donor CD8 T cells were purified by cell sorting. RNA was extracted from these cells and changes in gene expression were assessed using Affymetrix DNA microarray. FIG. 14A shows a graphical representation of several genes found to be down-regulated in Gal3−/− OT-1 over WT. FIG. 14B shows the relative units and fold change for selected genes.

Figure 15:
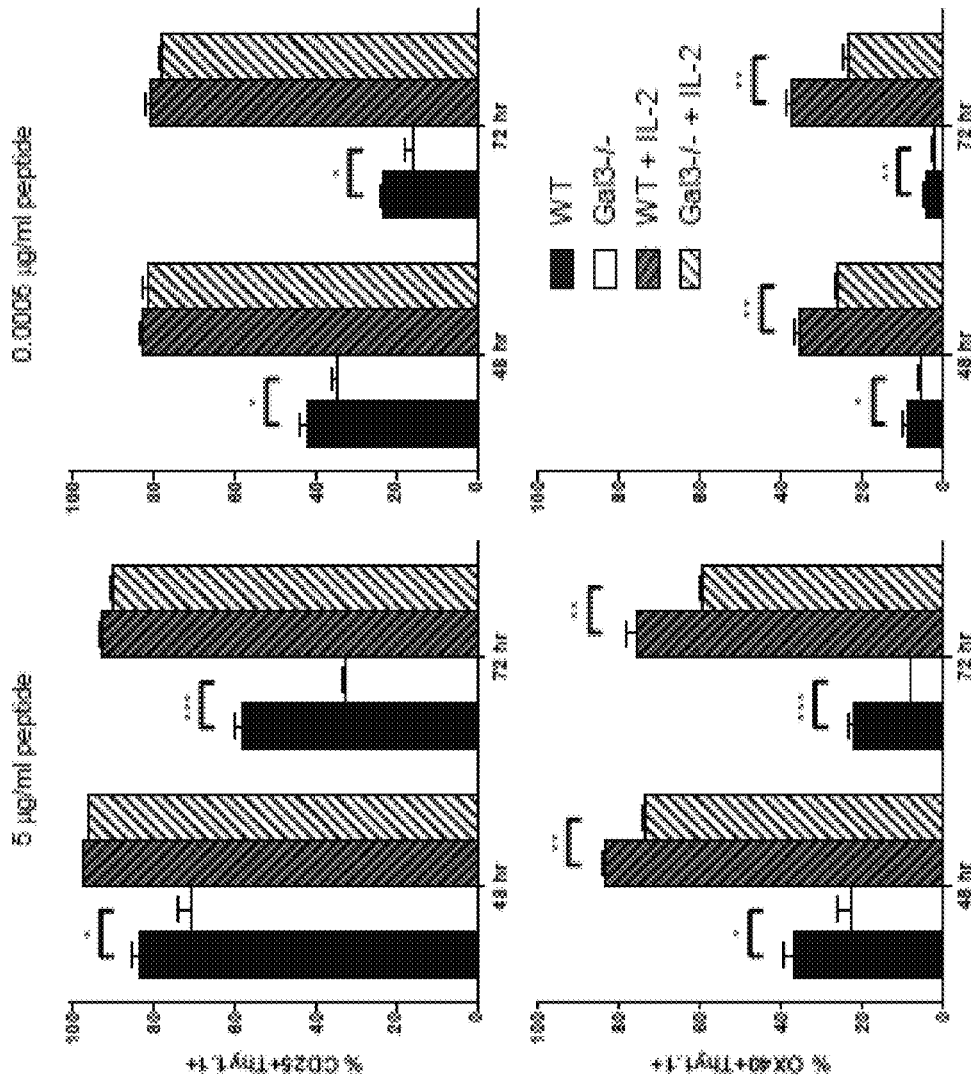
FIG. 15 shows the expression of CD25 (IL2-Ra) or OX40 by flow cytometry.

FIG. 15 shows that Galectin-deficient CD8 T-cells have reduced CD25 and OX40 expression following antigen stimulation. In vitro, naive purified wild-type or Gal3−/− OT-1 CD8 were stimulated with peptide-pulsed (either 5 or 0.0005 micrograms/ml) DC2.4 dendritic cells with or without IL-2 (100 ng/ml). Cells were harvested at 48 or 72 hrs later to examine expression of CD25 (IL-2Ra) or OX40 by flow cytometry.

Figure 16:
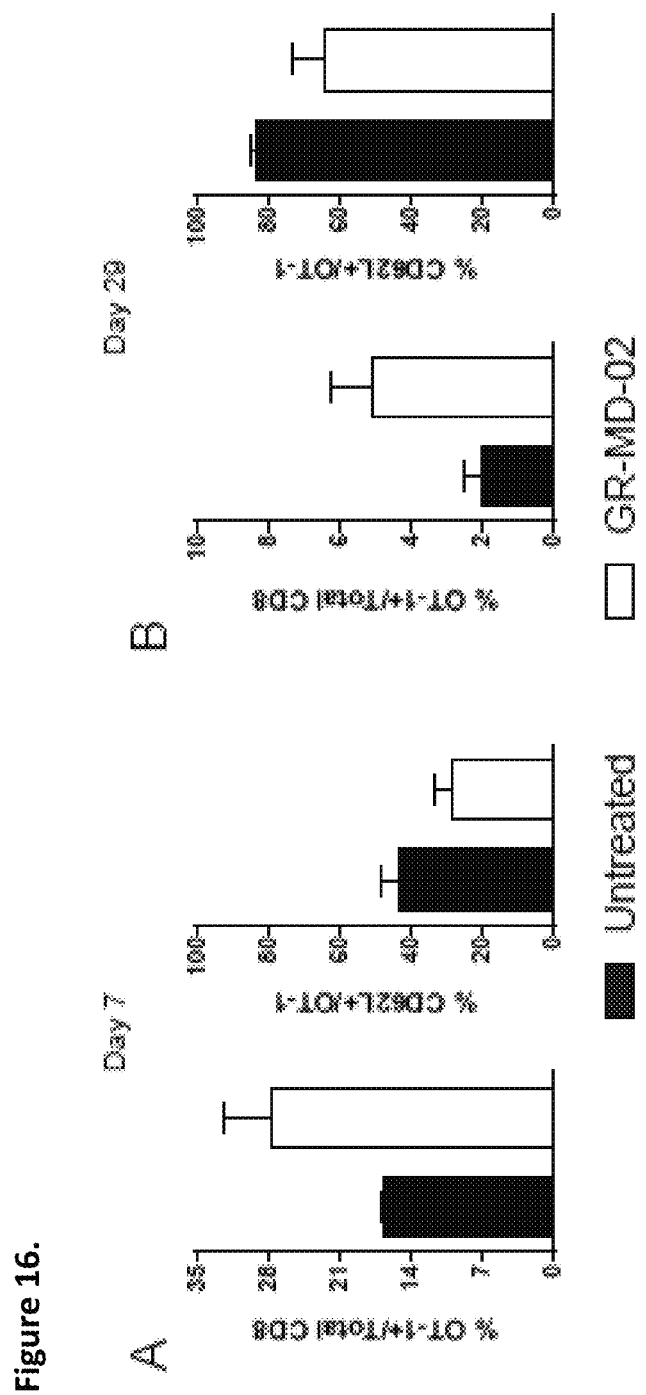
FIG. 16A shows the phenotype of donor cells in peripheral blood or spleen of untreated mice (black bars) or mice administered with a Gal-3 inhibitor GR-MD-02 at day 7.
FIG. 16B shows the phenotype of donor cells in peripheral blood or spleen of untreated mice (black bars) or mice administered with a Gal-3 inhibitor GR-MD-02 at day 29.

FIG. 16 shows that galectin-3 inhibition augments CD8 T cell effector function. Wild-type C57BL/6 mice received 3×10e6 naive WT OT-I CD8 T cells (iv) on day-1. Donor OT-I T cells. Gal-3 inhibitor, GR-MD-02 (a particular GA-RG) (white bars) (sq; d0, 1). Seven (FIG. 16A) or 29 (FIG. 16B) days later the phenotype of donor cells in the peripheral blood or spleen, respectively, was determined by flow cytometry. There were no differences between groups for expression of Ki-67, Granzyme B, or KLRG-1.

Figure 17:
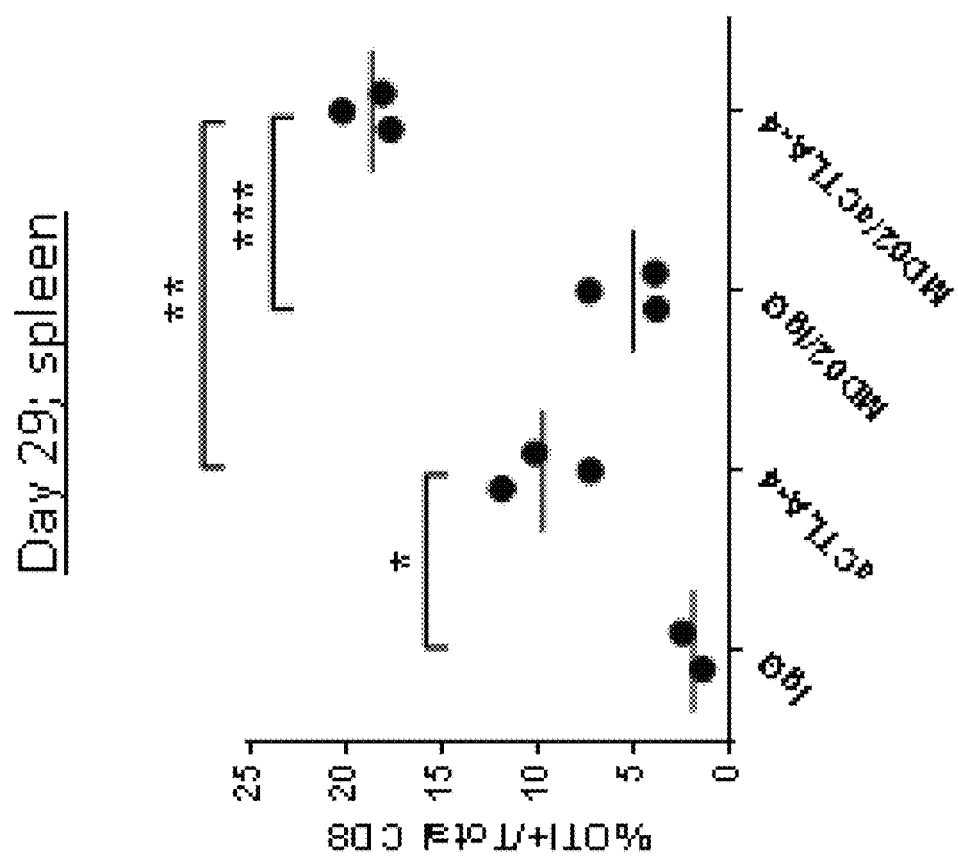
FIG. 17 depicts that galectin-3 inhibition in combination with anti-CTLA4 therapy augments the generation of antigen-specific memory CD8 T cells in the spleen versus anti-CTLA4 alone. GA-RG is labeled as MD02 in this figure.

FIG. 17 shows that galectin-3 inhibition with GA-RG (GR-MD-02) augments CD8 T-cell expansion when used in combination with anti-CTLA-4 in splenocytes isolated on day 29 as described above.

These studies show that endogenous galectin-3 deficiency decreased CD8 T cell proliferation and activation in response to antigen and decreased cytokine production.

Galectin-3 deficient CD8 T cells have reduced KLRG, CD25, IFNg, granzyme B, and FasL which are all increased in effector CD8.

Galectin-3 deficient CD8 T cells have reduced CD25 and OX40 expression in vitro. CD25 expression can be rescued by addition of IL-2, while OX40 expression cannot be rescued by addition of IL-2.

Galectin-3 inhibition in vivo using GA-RG (also called GR-MD-02) enhances CD8 T cell proliferation and activation in response to antigen.

Therefore, it is appears that inhibition of galectin-3 with an inhibitor that acts substantially or exclusively in the extracellular compartment has different effects than the complete lack of galectin-3 produced endogenously in T-cells.

While this invention has been particularly shown and described with references to preferred embodiments thereof, it will be understood by those skilled in the art that various changes in form and details may be made therein without departing from the scope of the invention. All publications, patents and sequence database entries mentioned herein are hereby incorporated by reference in their entirety as if each individual publication or patent was specifically and individually indicated to be incorporated by reference.

The invention claimed is:
1. A method for treating cancer comprising:
a) obtaining a composition for parenteral or enteral administration comprising:
(i) a galactoarabino-rhamnogalacturonate comprising a 1,4-linked galacturonic acid (GalA) comprising methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof,
wherein the 1,4-β-D-galactose and 1,5-α-L-arabinose residues are present in a 2:1 to a 3:1 ratio, and wherein the galactoarabino-rhamnogalacturonate has a methyl galacturonate to galacturonic acid ratio ranging from 2:1 to 1:2, and
(ii) a therapeutically effective amount of an immune modulatory agent in an acceptable pharmaceutical carrier, wherein the immune modulatory agent comprises a monoclonal antibody, a peptide, or an agent capable of binding to lymphocyte co-stimulatory ligands or receptors, to lymphocyte inhibitory ligands or receptors, to the tumor necrosis factor receptor (TNFR) superfamily of receptors or to the tumor necrosis factor receptor (TNFR) superfamily of ligands; and
b) administering to a subject in need thereof an effective dose of the composition, wherein the subject in need thereof has a malignant tumor, and wherein the effective dose of the composition increases by at least 10% the activation of CD8+ T-cells, resulting in at least one of:
at least 10% increase of tumor-antigen specific CD8+ T-cells,
at least 10% decrease in the malignant tumor size,
at least 10% decrease in size of metastases,
at least a 10% decrease in number of metastases,
an increase in survival of the subject, or
a reduction of total tumor burden,
when compared to a control subject treated with the therapeutically effective amount of the immune modulatory agent alone, and
wherein the malignant tumor is one of gastrointestinal cancer, pancreatic cancer, bile duct cancer, sarcoma, myosarcoma, breast cancer, lung cancer, head and neck cancer, mouth cancer, skin cancer, melanoma, kidney cancer, urinary tract cancer, prostate cancer, testicular cancer, ovarian cancer, endometrial cancer, neurological cancer, endocrine gland cancer, bone cancer, hematological cancers, multiple myeloma, and myelofibrosis.

2. The method of claim 1 wherein the step of administering results in at least a 50% reduction of the total tumor burden in the subject so as to treat cancer.

3. The method of claim 1 wherein in the step of obtaining the galactoarabino-rhamnogalacturonate, the 1,4-linked galacturonic acid comprising methyl galacturonate residues backbone represents between 55 to 85 molar percent of a total carbohydrate molar content, the branched heteropolymer of alternating α-1,2 linked rhamnose and α-1,4-linked GalA residues represents between 1 and 6 molar percent of the total carbohydrate molar content, the oligomer 1,4-β-D-galactose of the primary branching represents between 6 to 15 molar percent of the total carbohydrate molar content and the oligomer 1,5-α-L-arabinose of the primary branching represents between 2 to 8 molar percent of the total carbohydrate molar content, as characterized by gas chromatography/mass spectrometry.

4. The method of claim 1, wherein the galactoarabino-rhamnogalacturonate has an average molecular weight ranging from 20 kDa to 70 kDa.

5. The method of claim 1 wherein the immune modulatory agent comprises an anti-OX40, anti-CTLA-4, anti-PD-1 anti-PD-L1, anti PD-L2, antibody to 4-1BB/4-1BBL, antibody to LAG-3, or a combination thereof.

6. The method of claim 1 wherein the immune modulatory agent comprises a monoclonal antibody, peptide, or agent capable of binding to CD80, CD86, ICOS ligand or a combination thereof or a monoclonal antibody, peptide, agent capable of binding to CTLA-4, LAG-3 or combination thereof.

7. The method of claim 1 wherein the immune modulatory agent comprises a monoclonal antibody, peptide or other agent capable of binding to CD134, CD27, 4-1BB or combination thereof or capable of binding to OX40L, CD70, 4-1BBL or combination thereof.

8. The method of claim 1 wherein the immune modulatory agent comprises a recombinant OX40L or agonists of OX40.

9. The method of claim 1 wherein the immune modulatory agent comprises a monoclonal antibody capable of binding to PD-ligands.

10. The method of claim 1 wherein the immune modulatory agent comprises a monoclonal antibody, peptide or agent capable of modifying the activation or function of dendritic cells.

11. The method of claim 1 wherein the immune modulatory agent comprises a cancer vaccine, tumor-antigen directed vaccine or a vaccine capable of treating or preventing an infectious disease.

12. The method of claim 1 wherein the effective dose of the composition results in at least 10% increase of activation of CD8+ as measured by granzyme B expression.

13. The method of claim 1 wherein the effective dose of the composition results in at least 10% increase of activation of CD4+ as measured by Ki-67 expression.

14. The method of claim 1 wherein the effective dose of the composition results in at least 10% increase of GR-1 negative/CD11b positive cells.

15. The method of claim 1 wherein the effective dose of the composition results in at least 10% decrease of GR-1 intermediate/CD11b positive cells.

16. The method of claim 1 wherein the galactoarabino-rhamnogalacturonate inhibits galectin-3 function and augments CD8+ T cell expansion and effector function.

17. The method of claim 1 wherein when the composition is administered, the composition provides for a synergistic reduction of tumor size and/or increase in survival when compared to the reduction of the tumor size and/or increase in survival provided by the administration of the immune modulatory agent without the galactoarabino-rhamnogalacturonate.

* * * * *

UNITED STATES PATENT AND TRADEMARK OFFICE
CERTIFICATE OF CORRECTION

| | |
|---|---|
| PATENT NO. | : 9,872,909 B2 |
| APPLICATION NO. | : 14/029505 |
| DATED | : January 23, 2018 |
| INVENTOR(S) | : Peter G. Traber et al. |

Page 1 of 1

It is certified that error appears in the above-identified patent and that said Letters Patent is hereby corrected as shown below:

On the Title Page

In the Assignees please replace "(73) Assignees: Galeotin Therapeutics, Inc., Norcross, GA (US); Providence Health & Services-Oregon, Portland, OR (US)"
With:
"(73) Assignees: Galectin Therapeutics, Inc., Norcross, GA (US); Providence Health & Services-Oregon, Portland, OR (US)"

Signed and Sealed this
Tenth Day of July, 2018

Andrei Iancu
*Director of the United States Patent and Trademark Office*